(12) United States Patent
Naldini et al.

(10) Patent No.: US 8,652,837 B2
(45) Date of Patent: *Feb. 18, 2014

(54) METHOD AND MEANS FOR PRODUCING HIGH TITER, SAFE, RECOMBINANT LENTIVIRUS VECTORS

(75) Inventors: Luigi Naldini, San Carlos, CA (US); Thomas Dull, San Francisco, CA (US); Anatoly Bukovsky, Bellevue, WA (US); Deborah A. Farson, Oakland, CA (US); Rochelle Witt, San Francisco, CA (US)

(73) Assignee: GBP IP, LLC, Greenwich, CT (US)

( * ) Notice: Subject to any disclaimer, the term of this patent is extended or adjusted under 35 U.S.C. 154(b) by 1019 days.

This patent is subject to a terminal disclaimer.

(21) Appl. No.: 11/781,094

(22) Filed: Jul. 20, 2007

(65) Prior Publication Data

US 2008/0241929 A1 Oct. 2, 2008

Related U.S. Application Data

(63) Continuation of application No. 10/031,639, filed as application No. PCT/US00/11097 on Apr. 26, 2000, now Pat. No. 7,250,299.

(60) Provisional application No. 60/131,671, filed on Apr. 29, 1999.

(51) Int. Cl.
*C12N 15/00* (2006.01)
*C12N 15/85* (2006.01)

(52) U.S. Cl.
USPC ..................................... 435/320.1; 435/325

(58) Field of Classification Search
None
See application file for complete search history.

(56) References Cited

U.S. PATENT DOCUMENTS

| | | | |
|---|---|---|---|
| 5,503,974 A | 4/1996 | Gruber et al. | |
| 5,583,022 A | 12/1996 | Heidmann et al. | |
| 5,589,362 A | 12/1996 | Bujard et al. | |
| 5,591,579 A | 1/1997 | Olivo et al. | |
| 5,614,404 A | 3/1997 | Mazzara et al. | |
| 5,650,309 A | 7/1997 | Wong-Staal et al. | |
| 5,665,577 A | 9/1997 | Sodroski et al. | |
| 5,681,746 A | 10/1997 | Bodner et al. | |
| 5,686,279 A | 11/1997 | Finer et al. | |
| 5,693,508 A | 12/1997 | Chang | |
| 5,716,613 A | 2/1998 | Guber et al. | |
| 5,716,826 A | 2/1998 | Gruber et al. | |
| 5,739,118 A | 4/1998 | Carrano et al. | |
| 5,747,307 A | 5/1998 | Lever et al. | |
| 5,750,383 A | 5/1998 | Blissard et al. | |
| 5,994,136 A | 11/1999 | Naldini et al. | |
| 6,013,516 A | 1/2000 | Verma et al. | |
| 6,165,782 A | 12/2000 | Naldini et al. | |
| 6,207,455 B1 | 3/2001 | Chang | |
| 6,312,682 B1 | 11/2001 | Kingsman et al. | |
| 6,365,150 B1 | 4/2002 | Leboulch et al. | |
| 6,428,953 B1 | 8/2002 | Naldini et al. | |
| 6,924,144 B2 | 8/2005 | Naldini et al. | |
| 7,083,981 B2 * | 8/2006 | Naldini et al. | ................. 435/456 |
| 2003/0104611 A1 | 6/2003 | Johnston et al. | |

FOREIGN PATENT DOCUMENTS

| | | |
|---|---|---|
| AU | 712951 | 2/1997 |
| EP | 0759471 A1 | 2/1997 |
| WO | WO 95/30755 | 11/1995 |
| WO | WO 95/32300 | 11/1995 |
| WO | WO 96/14332 | 5/1996 |
| WO | WO 97/07225 | 2/1997 |
| WO | WO 97/12622 | 4/1997 |
| WO | WO 97/20052 | 6/1997 |
| WO | WO 98/12314 | 3/1998 |
| WO | WO 98/17816 | 4/1998 |
| WO | WO 99/04026 | 1/1999 |
| WO | WO 99/31251 | 6/1999 |

OTHER PUBLICATIONS

Lindemann et al. Versatile retrovirus vector systems for regulated gene expression in vitro and in vivo. Mol Med. Jul. 1997; 3(7): 466-476.*
Wiznerowicz et al. Double-copy bicistronic retroviral vector platform for gene therapy and tissue engineering: application to melanoma vaccine development. Gene Ther. Oct. 1997;4(10):1061-8.*
Berkhout et al., 1989, "Tat Transactivates the Human Immunodeficiency Virus Through a Nascent RNA Target", Cell; 59:273-82.
Blomer et al., 1997, "Highly Efficient and Sustained Gene Transfer in Adult Neurons with a Lentivirus Vector", J. Virol.; 71(9):6641-49.
Bukovsky et al. 1999, "Interaction of Human Immunodeficiency Virus-Derived Vectors with Wild-Type Virus in Transduced Cells", J. Virol.; 73(8):7087-92.
Chang et al., 1999, "Efficacy and Safety Analyses of a Recombinant Human Immunodeficiency Virus Type I Derived Vector System", Gene Therapy: 6:715-728.
Coffin et al., 1996, "*Retroviridae. The Viruses and Their Replication*". 3$^{rd}$ Edition, Fields et al., eds., Lipincott-Raven Publishers, Philadelphia, PA; Ch. 26:763-843.
Das et al., 1997, "A conserved hairpin motif in the R-U5 region of the human immunodeficiency virus type 1 RNA genome is essential for replication", J. Virol.; 71(3):2346-56.
Dull et al., 1998, "A Third Generation Lentivirus Vector with a Conditional Packaging System", J. Virol.; 72(11):8463-71.
Elder et al., 1995. "Feline Immunodeficiency Virus as a Model for Development of Molecular Approaches to Intervention Strategies Against Lentivirus Infections", Adv. Virus Res.; 45:225-247.
Farson et al., 1999, "Large-Scale Manufacturing of Safe and Efficient Retrovirus Packaging Liners for use in Immunotherapy Protocols", J. Gene Med.; 1:195-209.
Ferry et al., 1998, "Liver-Directed Gene Transfer Vectors", Human Gene Therapy; 9:1975-81.

(Continued)

Primary Examiner — Michele K Joike
(74) Attorney, Agent, or Firm — Jones Day

(57) ABSTRACT

Lentiviral vectors modified at the 5' LTR or both the 5' and 3' LTR are useful in the production of recombinant lentivirus vectors (See the Figure). Such vectors can be produced in the absence of a functional tat gene. Multiple transformation of the host cell with the vector carrying the transgene enhances virus production. The vectors can contain inducible or conditional promoters.

21 Claims, 15 Drawing Sheets

(56) References Cited

OTHER PUBLICATIONS

Gasmi et al., 1999, "Requirements for Efficient Production and Transduction of Human Immunodeficiency Virus Type 1-Based Vectors", J. Virol.; 73(3):1828-34.

Kafri et al., 1997, "Sustained Expression of Genes Delivered Directly into Liver and Muscle by Lintiviral Vectors", Nature Genetics; 17:314-17.

Kalpana et al., 1999, "Retroviral Vectors for Liver-Directed Gene Therapy", Seminars in Liver Disease; 19(1)27-37.

Kim et al., 1998, "Construction of Retroviral Vectors with Improved Safety, Gene Expression, and Versatility", J. Virol.; 72(2):994-1004.

Lisziewicz et al., 1993, "Inhibition of Human Immunodeficiency Virus Type 1 Replication by Regulated Expression of a Polymeric Tat Activation Response RNA Decoy as a Strategy for Gene Therapy in AIDS", Proc. Natl. Acad. Sci. USA; 90:8000-04.

Miyoshi et al., 1998, "Development of a Self-Inactivating Lentivirus Vector", J. Virol.; 72(10):8150-57.

Naldini et al., 1996, "Efficient Transfer, Integration, and Sustained Long-Term Expression of the Transgene in Adul Rat Brains Injected with a Lentiviral Vector", Proc. Natl. Acad. Sci. USA; 93:11382-88.

Naldini et al., 1996, In Vivo Gene Delivery and Stable Transduction of Nondiving Cells by a Lentiviral Vector; Science; 272:263-67.

Ory et al., 1996, "A Stable Human-Derived Packaging Cell Line for Production of High Titer Retrovirus/Vesicular Stomatitias Virus G Pseudotypes", Proc. Natl. Acad. Sci. USA; 93:11400-06.

Park et al., 2000, "Efficient lentiviral transduction of liver requires cell cycling in vivo", Nature Genetics; 24:49-52.

Park et al., 2000, "Therapeutic levels of human factor VIII and IX using HIV-1 based lentiviral vectors in mouse liver", Blood; 96(3):1173-76.

Robinson et al., 1995, "Retroviral vector with a CMV-IE/HIV-TAR hybrid LTR gives high basal expression levels and is up-regulated by HIV-1 Tat", Gene Therapy; 2(4):269-78.

Schneider et al., 1997, "Inactivation of the Human Immunodeficiency Virus Type I Inhibitory Elements Allows Rev-Independent Expression of Gag and Gag/Protease and Particle Formation", J. Virol.; 71(7):4892-4903.

Shinya et al., 1994, "A safe HIV vectors packaging system using the U3 deficient LTR", Abstract, Gene Therapy Meeting; p. 150.

Srinivasakumar et al., 1997, "The effect of viral regulatory protein expression on gene delivery by human immunodeficiency virus type 1 vectors produced in stable packaging cell lines", J. Virol.; 71(8):5841-48.

Xu et al., 2001, "Generation of a stable cell line producing high-titer self-inactivating lentiviral vectors", Molecular Therapy; 3(1):97-104.

Zern et al., 1997, "Hepatic Drug Delivery and Gene Therepy", Hepatology; 25(2):484-491.

Zufferey et al., 1997, "Multiply Attenuated Lentiviral Vector Achieves Efficient Gene Delivery in Vivo", Nature Biotechnology; 15:871-75.

Zufferey et al., 1998, "Self-Inactivating Lentivirus Vector for Safe and Efficient in Vivo Gene Delivery", J. Virol.; 72(12)9873-80.

The International Search Report, PCT/US00/11097, dated Aug. 11, 2000.

The International Preliminary Examination Report, PCT/US00/11097, dated Jan. 22, 2001.

European Search Report. EP 07012545, dated Sep. 4, 2007.

Supplementary European Search Report, EP 00926354, dated Apr. 30, 2002.

Supplementary European Search Report, EP 98962894, dated Aug. 18, 2004.

* cited by examiner

SEQUENCE LISTING

<160> NUMBER OF SEQ ID NOS: 52

<210> SEQ ID NO 1
<211> LENGTH: 10
<212> TYPE: RNA
<213> ORGANISM: HIV-1

<400> SEQUENCE: 1
gacuggugag                                                           10

<210> SEQ ID NO 2
<211> LENGTH: 77
<212> TYPE: DNA
<213> ORGANISM: Artificial Sequence
<220> FEATURE:
<223> OTHER INFORMATION: oligonucleotide linker

<400> SEQUENCE: 2
gggactggtg agtgaattcg agatctgccg ccgccatggg tgcgagagcg tcagtattaa    60
gcgggggaga attagat                                                   77

<210> SEQ ID NO 3
<211> LENGTH: 81
<212> TYPE: DNA
<213> ORGANISM: Artificial Sequence
<220> FEATURE:
<223> OTHER INFORMATION: oligonucleotide linker

<400> SEQUENCE: 3
cgatctaatt ctcccccgct taatactgac gctctcgcac ccatggcggc ggcagatctc    60
gaattcactc accagtcccg c                                              81

<210> SEQ ID NO 4
<211> LENGTH: 65
<212> TYPE: DNA
<213> ORGANISM: Artificial Sequence
<220> FEATURE:
<223> OTHER INFORMATION: oligonucleotide

<400> SEQUENCE: 4
ccatcgatca cgagactagt cctacgtatc cccggggacg ggatccgcgg aattccgttt    60
aagac                                                                65

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
ttataatgtc aaggcctctc                                                20

<210> SEQ ID NO 6
<211> LENGTH: 26
<212> TYPE: DNA
<213> ORGANISM: Artificial Sequence
<220> FEATURE:
<223> OTHER INFORMATION: primer

<400> SEQUENCE: 6
gcggccgcag gagctttgtt ccttgg                                         26

```
<210> SEQ ID NO 7
<211> LENGTH: 18
<212> TYPE: DNA
<213> ORGANISM: Artificial Sequence
<220> FEATURE:
<223> OTHER INFORMATION: primer

<400> SEQUENCE: 7
tacgtaggac tagtctcg                                                       18

<210> SEQ ID NO 8
<211> LENGTH: 12
<212> TYPE: DNA
<213> ORGANISM: Artificial Sequence
<220> FEATURE:
<223> OTHER INFORMATION: synthetic oligonucleotide

<400> SEQUENCE: 8
ttgcggccgc aa                                                             12

<210> SEQ ID NO 9
<211> LENGTH: 15
<212> TYPE: DNA
<213> ORGANISM: Artificial Sequence
<220> FEATURE:
<223> OTHER INFORMATION: primer

<400> SEQUENCE: 9
ccactgctta agcct                                                          15

<210> SEQ ID NO 10
<211> LENGTH: 37
<212> TYPE: DNA
<213> ORGANISM: Artificial Sequence
<220> FEATURE:
<223> OTHER INFORMATION: primer

<400> SEQUENCE: 10
caaaattttt ggcgtactca tcagtcgccg cccctcg                                  37

<210> SEQ ID NO 11
<211> LENGTH: 74
<212> TYPE: DNA
<213> ORGANISM: Artificial Sequence
<220> FEATURE:
<223> OTHER INFORMATION: oligonucleotide linker

<400> SEQUENCE: 11
aattgccgca ttgcagagat attgtattta agtgcctagc tcgatacaat aaacgggtct         60
ctctggttag acca                                                           74

<210> SEQ ID NO 12
<211> LENGTH: 74
<212> TYPE: DNA
<213> ORGANISM: Artificial Sequence
<220> FEATURE:
<223> OTHER INFORMATION: oligonucleotide linker

<400> SEQUENCE: 12
gatctggtct aaccagagag acccgtttat tgtatcgagc taggcactta aatacaatat         60
ctctgcaatg cggc                                                           74

<210> SEQ ID NO 13
<211> LENGTH: 50
<212> TYPE: DNA
```

<213> ORGANISM: Artificial Sequence
<220> FEATURE:
<223> OTHER INFORMATION: oligonucleotide linker

<400> SEQUENCE: 13
aattggaggc gtggcctggg cgggactggg gagtggcgag ccctcagatc        50

<210> SEQ ID NO 14
<211> LENGTH: 43
<212> TYPE: DNA
<213> ORGANISM: Artificial Sequence
<220> FEATURE:
<223> OTHER INFORMATION: oligonucleotide linker

<400> SEQUENCE: 14
ctgagggctc gccactcccc agtcccgccc aggccacgcc tcc              43

<210> SEQ ID NO 15
<211> LENGTH: 14
<212> TYPE: DNA
<213> ORGANISM: Artificial Sequence
<220> FEATURE:
<223> OTHER INFORMATION: plasmid

<400> SEQUENCE: 15
gatatgatca gatc                                              14

<210> SEQ ID NO 16
<211> LENGTH: 7
<212> TYPE: DNA
<213> ORGANISM: Artificial Sequence
<220> FEATURE:
<223> OTHER INFORMATION: plasmid

<400> SEQUENCE: 16 ctgatca                                                       7

<210> SEQ ID NO 17
<211> LENGTH: 23
<212> TYPE: DNA
<213> ORGANISM: Artificial Sequence
<220> FEATURE:
<223> OTHER INFORMATION: oligonucleotide linker

<400> SEQUENCE: 17
gatatgatca gagccctcag atc                                    23

<210> SEQ ID NO 18
<211> LENGTH: 16
<212> TYPE: DNA
<213> ORGANISM: Artificial Sequence
<220> FEATURE:
<223> OTHER INFORMATION: oligonucleotide linker

<400> SEQUENCE: 18
ctgagggctc tgatca                                            16

<210> SEQ ID NO 19
<211> LENGTH: 56
<212> TYPE: DNA
<213> ORGANISM: Artificial Sequence
<220> FEATURE:
<223> OTHER INFORMATION: oligonucleotide linker

<400> SEQUENCE: 19
gatatgatca ggaggcgtgg cctgggcggg actggggagt ggcgagccct cagatc  56

```
<210> SEQ ID NO 20
<211> LENGTH: 49
<212> TYPE: DNA
<213> ORGANISM: Artificial Sequence
<220> FEATURE:
<223> OTHER INFORMATION: oligonucleotide linker

<400> SEQUENCE: 20
ctgagggctc gccactcccc agtcccgccc aggccacgcc tcctgatca          49

<210> SEQ ID NO 21
<211> LENGTH: 43
<212> TYPE: DNA
<213> ORGANISM: Artificial Sequence
<220> FEATURE:
<223> OTHER INFORMATION: oligonucleotide linker

<400> SEQUENCE: 21
catgggtgcg agagcgtcag tattaagcgg gggagaatta gat                43

<210> SEQ ID NO 22
<211> LENGTH: 41
<212> TYPE: DNA
<213> ORGANISM: Artificial Sequence
<220> FEATURE:
<223> OTHER INFORMATION: oligonucleotide linker

<400> SEQUENCE: 22
cgatctaatt ctcccccgct taatactgac gctctcgcac c                  41

<210> SEQ ID NO 23
<211> LENGTH: 12
<212> TYPE: DNA
<213> ORGANISM: Artificial Sequence
<220> FEATURE:
<223> OTHER INFORMATION: oligonucleotide linker

<400> SEQUENCE: 23
agcttccgcg ga                                                  12

<210> SEQ ID NO 24
<211> LENGTH: 12
<212> TYPE: DNA
<213> ORGANISM: Artificial Sequence
<220> FEATURE:
<223> OTHER INFORMATION: oligonucleotide linker

<400> SEQUENCE: 24
gatctccgcg ga                                                  12

<210> SEQ ID NO 25
<211> LENGTH: 63
<212> TYPE: DNA
<213> ORGANISM: Artificial Sequence
<220> FEATURE:
<223> OTHER INFORMATION: oligonucleotide linker

<400> SEQUENCE: 25
aattcgagat ctgccgccgc catgggagcc cgggccagcg tcctgtctgg aggggagctg   60
gac                                                                63

<210> SEQ ID NO 26
<211> LENGTH: 61
<212> TYPE: DNA
<213> ORGANISM: Artificial Sequence
<220> FEATURE:
```

```
<223> OTHER INFORMATION: oligonucleotide linker

<400> SEQUENCE: 26
cggtccagct cccctccaga caggacgctg gcccgggctc ccatggcggc ggcagatctc    60
g                                                                    61

<210> SEQ ID NO 27
<211> LENGTH: 42
<212> TYPE: DNA
<213> ORGANISM: Artificial Sequence
<220> FEATURE:
<223> OTHER INFORMATION: oligonucleotide linker

<400> SEQUENCE: 27
aattcgagat ctgccgccgc catgggagcc cgggccagcg tc                        42

<210> SEQ ID NO 28
<211> LENGTH: 43
<212> TYPE: DNA
<213> ORGANISM: Artificial Sequence
<220> FEATURE:
<223> OTHER INFORMATION: oligonucleotide linker

<400> SEQUENCE: 28
ctagagacgc tggcccgggc tcccatggcg gcggcagatc tcg                       43

<210> SEQ ID NO 29
<211> LENGTH: 77
<212> TYPE: DNA
<213> ORGANISM: Artificial Sequence
<220> FEATURE:
<223> OTHER INFORMATION: oligonucleotide linker

<400> SEQUENCE: 29
aattcacgcg tgccgccacc atggcaggaa gaagcggaga cagcgacgaa gacctcctcg    60
cggccgccag tagctgt                                                   77

<210> SEQ ID NO 30
<211> LENGTH: 77
<212> TYPE: DNA
<213> ORGANISM: Artificial Sequence
<220> FEATURE:
<223> OTHER INFORMATION: oligonucleotide linker

<400> SEQUENCE: 30
aattacagct actggcggcc gcgaggaggt cttcgtcgct gtctccgctt cttcctgcca    60
tggtggcggc acgcgtg                                                   77

<210> SEQ ID NO 31
<211> LENGTH: 10
<212> TYPE: DNA
<213> ORGANISM: Artificial Sequence
<220> FEATURE:
<223> OTHER INFORMATION: oligonucleotide linker

<400> SEQUENCE: 31
ggccattgac                                                           10

<210> SEQ ID NO 32
<211> LENGTH: 10
<212> TYPE: DNA
<213> ORGANISM: Artificial Sequence
<220> FEATURE:
<223> OTHER INFORMATION: oligonucleotide linker
```

```
<400> SEQUENCE: 32
tcgagtcaat                                                          10

<210> SEQ ID NO 33
<211> LENGTH: 38
<212> TYPE: DNA
<213> ORGANISM: Artificial Sequence
<220> FEATURE:
<223> OTHER INFORMATION: primer

<400> SEQUENCE: 33
tctagaggat ccgtcgacaa tcaacctctg gattacaa                            38

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
gagctcgaat tccaggcggg gaggcggccc aa                                  32

<210> SEQ ID NO 35
<211> LENGTH: 10
<212> TYPE: DNA
<213> ORGANISM: Artificial Sequence
<220> FEATURE:
<223> OTHER INFORMATION: linker

<400> SEQUENCE: 35
gatcccgggc                                                          10

<210> SEQ ID NO 36
<211> LENGTH: 10
<212> TYPE: DNA
<213> ORGANISM: Artificial Sequence
<220> FEATURE:
<223> OTHER INFORMATION: linker

<400> SEQUENCE: 36
tcgagcccgg                                                          10

<210> SEQ ID NO 37
<211> LENGTH: 21
<212> TYPE: DNA
<213> ORGANISM: Artificial Sequence
<220> FEATURE:
<223> OTHER INFORMATION: linker

<400> SEQUENCE: 37
gtacccgggt cgagtaggct t                                             21

<210> SEQ ID NO 38
<211> LENGTH: 21
<212> TYPE: DNA
<213> ORGANISM: Artificial Sequence
<220> FEATURE:
<223> OTHER INFORMATION: linker

<400> SEQUENCE: 38
gatcaagcct actcgacccg g                                             21

<210> SEQ ID NO 39
<211> LENGTH: 21
<212> TYPE: DNA
```

```
<213> ORGANISM: Artificial Sequence
<220> FEATURE:
<223> OTHER INFORMATION: primer

<400> SEQUENCE: 39
catcaggcca tatcacctag a                                            21

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
gtactagtag ttcctgctat gt                                           22

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
ctgctgacat cgagcttgct aca                                          23

<210> SEQ ID NO 42
<211> LENGTH: 23
<212> TYPE: DNA
<213> ORGANISM: Artificial Sequence
<220> FEATURE:
<223> OTHER INFORMATION: primer

<400> SEQUENCE: 42
ctagctccct gcttgcccat act                                          23

<210> SEQ ID NO 43
<211> LENGTH: 68
<212> TYPE: DNA
<213> ORGANISM: Artificial Sequence
<220> FEATURE:
<223> OTHER INFORMATION: primer

<400> SEQUENCE: 43
ccatcgatgg actagtccta cgtatccccg gggacgggat ccgcggaatt ccgtttaaga    60
ccaatgac                                                           68

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
ttataatgtc aaggcctctc                                              20

<210> SEQ ID NO 45
<211> LENGTH: 43
```

```
<212> TYPE: DNA
<213> ORGANISM: Artificial Sequence
<220> FEATURE:
<223> OTHER INFORMATION: linker

<400> SEQUENCE: 45
catgggtgcg agagcgtcag tattaagcgg gggagaatta gat        43

<210> SEQ ID NO 46
<211> LENGTH: 41
<212> TYPE: DNA
<213> ORGANISM: Artificial Sequence
<220> FEATURE:
<223> OTHER INFORMATION: linker

<400> SEQUENCE: 46
cgatctaatt ctcccccgct taatactgac gctctcgcac c          41

<210> SEQ ID NO 47
<211> LENGTH: 12
<212> TYPE: DNA
<213> ORGANISM: Artificial Sequence
<220> FEATURE:
<223> OTHER INFORMATION: linker

<400> SEQUENCE: 47
agcttccgcg ga                                          12

<210> SEQ ID NO 48
<211> LENGTH: 12
<212> TYPE: DNA
<213> ORGANISM: Artificial Sequence
<220> FEATURE:
<223> OTHER INFORMATION: linker

<400> SEQUENCE: 48
gatctccgcg ga                                          12

<210> SEQ ID NO 49
<211> LENGTH: 10
<212> TYPE: DNA
<213> ORGANISM: Artificial Sequence
<220> FEATURE:
<223> OTHER INFORMATION: linker

<400> SEQUENCE: 49
gatcccgggc                                             10

<210> SEQ ID NO 50
<211> LENGTH: 10
<212> TYPE: DNA
<213> ORGANISM: Artificial Sequence
<220> FEATURE:
<223> OTHER INFORMATION: linker

<400> SEQUENCE: 50
tcgagcccgg                                             10

<210> SEQ ID NO 51
<211> LENGTH: 21
<212> TYPE: DNA
<213> ORGANISM: Artificial Sequence
<220> FEATURE:
<223> OTHER INFORMATION: linker

<400> SEQUENCE: 51
gtacccgggt cgagtaggct t                                21
```

```
<210> SEQ ID NO 52
<211> LENGTH: 21
<212> TYPE: DNA
<213> ORGANISM: Artificial Sequence
<220> FEATURE:
<223> OTHER INFORMATION: linker

<400> SEQUENCE: 52
gatcaagcct actcgacccg g                                              21
```

METHOD AND MEANS FOR PRODUCING HIGH TITER, SAFE, RECOMBINANT LENTIVIRUS VECTORS

This application is a continuation of application Ser. No. 10/031,639, filed May 9, 2002, now U.S. Pat. No. 7,250,299, which is a national application based on PCT/US00/1097, filed Apr. 26, 2000, which claims the benefit of provisional application No. 60/131,671, filed Apr. 29, 1999.

FIELD OF THE INVENTION

The invention relates to novel lentiviral packaging vectors, transfer vectors carrying a foreign gene of interest, stable packaging cell lines, stable producer cell lines and the use thereof for producing recombinant lentivirus in mammalian cells.

BACKGROUND OF THE INVENTION

Retrovirus vectors are a common tool for gene delivery (Miller, Nature (1992) 357: 455-460). The biology of retroviral proliferation enables such a use. Typically, wild type full length retroviral mRNA's serve both as a template for synthesis of viral proteins and as the viral genome. Such mRNA's encompass a region called the encapsidation signal which binds certain viral proteins thereby ensuring specific association of that mRNA with the produced virions. On infection of the target cell, reverse transcription of the retroviral mRNA into double stranded proviral DNA occurs. The retroviral enzyme, integrase, then binds to both long terminal repeats (LTR) which flank the proviral DNA and subsequently catalyzes the integration thereof into the genomic DNA of the target cell. Integrated proviral DNA serves as the template for generation of new full-length retroviral mRNA's.

Retroviral vectors have been tested and found to be suitable delivery vehicles for the stable introduction of a variety of genes of interest into the genomic DNA of a broad range of target cells, a process known as transduction of the cells with the gene of interest. The ability of retrovirus vectors to deliver an unrearranged, single copy gene into a broad range of, for example, rodent, primate and human somatic cells makes retroviral vectors well suited for transferring genes to a cell.

A primary approach in retrovirus-derived vector design relies on removal of the encapsidation signal and sequences coding the LTR's from the viral genome without affecting viral protein expression and transfer of such sequences to the construct including a nucleic acid coding the gene of interest, sometimes called the transfer vector.

A useful adjunct for producing recombinant retroviral vectors are packaging cell lines which supply in trans the proteins necessary for producing infectious virions, but those cells are incapable of packaging endogenous viral genomic nucleic acids (Watanabe & Temin, Molec. Cell. Biol. (1983) 3: 2241-2249; Mann et al., Cell (1983) 33; 153-159; and Embretson & Temin, J. Virol. (1987) 61; 2675-2683). Expression in the vector producer cells of both viral core proteins, which comprise the virion particle, and mRNA containing LTR, encapsidation sequences and the gene of interest, results in release by the cells of particles which phenotypically resemble parental retrovirus, but carry the gene of interest instead of the viral genome. Such particles will integrate the gene of interest but not the viral DNA into the genome of target cells.

A consideration in the construction of retroviral packaging cell lines is the production of high titer vector supernatants free of recombinant replication competent retrovirus (RCR), which have been shown to produce T cell lymphomas in rodents (Cloyd et al., J. Exp. Med. (1980) 151: 542-552) and in primates (Donahue et al., J. Exp. Med. (1992) 176: 1125-1135).

In the vector producing cells, restoration of the physical association of LTR and encapsidation sequences with the sequences coding the viral proteins may lead to the emergence of RCR capable of self amplification. Generation of recombinant viruses during vector production is highly undesirable for several reasons. First, the recombinant mRNA may compete with the transgene mRNA for encapsidation into virions thereby decreasing the number of transgenes per vector particle made by producer cells. That competition, as well as amplification of such recombinants in producer cells, may lead to the exponential loss of vector transduction potential.

Second, such recombinants, if undetected during vector production, may be introduced unintentionally to the vector recipients. There, transfer of the recombinant genome to the host may cause otherwise avoidable toxicity or an immune reaction to the transduced cells. Importantly, viral recombinants may be pathogenic or may evolve into pathogens on additional rounds of amplification and/or through additional events of recombination with endogenous sequences of the host cells (such as endogenous retroviral sequences).

Recombinant retrovirus could be generated at the DNA or mRNA level. DNA recombination may take place if plasmid constructs independently coding for packaging and transfer vector functions are mixed and cotransfected in an attempt to create transient producer cells. To decrease the chance of recombination at the DNA level, the constructs could be introduced into cells one after another with concurrent selection of clones after each construct is associated stably with the cellular genome. Somatic cells dividing mitotically generally do not undergo crossing over between homologous chromosomes and since each vector construct association is expected to be integrated randomly into the genomic DNA, the likelihood of close association and therefore the chance of recombination is low.

Recombination at the mRNA level may take place during reverse transcription when both packaging mRNA and transfer vector mRNA (even when generated by separated expression constructs) become co-encapsidated into viral particles. The retroviral enzyme reverse transcriptase (RT) uses mRNA as template for DNA synthesis. Also, RT is known to switch between or away templates. Thus, if two different mRNA's are present within a viral particle, when combined, a single DNA unit could be synthesized by the RT as the result of template switching.

One approach to minimize the likelihood of generating RCR in packaging cells is to divide the packaging functions into two or more genomes, for example, one which expresses the gag and pol gene products and the other which expresses the env gene product (Bosselman et al., Molec. Cell. Biol. (1987) 7: 1797-1806, Markowitz et al. J. Virol. (1988) 62: 1120-1124; and Danos & Mulligan, Proc. Natl. Acad. Sci. (1988) 85, 6460-6464). That approach minimizes the ability for co-packaging and subsequent transfer of the two or more genomes, as well as significantly decreasing the frequency of recombination due to the presence of multiple retroviral genomes in the packaging cell to produce RCR.

The rationale behind the approach of splitting the packaging functions is that multiple recombination events must occur to generate RCR. That approach, however, does not decrease the chance of individual recombination events. Therefore partial-recombinants incapable of amplification could be generated. To monitor emergence of such partial recombinants, novel complementing detection systems must be designed.

In the event recombinants arise, mutations (Danos & Mulligan, supra) or deletions (Boselman et al., supra; and Markowitz et al., supra) within vector constructs can be configured such that in the event recombinants arise, those will be rendered non-functional.

In addition, deletion of the 3' LTR on both packaging constructs further reduces the ability to form functional recombinants.

It was demonstrated previously for many biological systems that the frequency of recombination between two genetic elements is directly proportional to the extent of homologous sequences. Thus, another approach is to minimize the extent of sequence homology between and amongst the vectors. Technical difficulties associated with minimization of the homologous sequences between transfer vector and packaging constructs can be explained by the fact that some essential genetic elements could not be removed from at least one of the constructs without significant loss of transduction potential.

Lentiviruses are complex retroviruses which, in addition to the common retroviral genes gag, pol and env, contain other genes with regulatory or structural function. The higher complexity enables the lentivirus to modulate the life cycle thereof, as in the course of latent infection.

Lentiviruses have attracted the attention of gene therapy investigators because of the ability to integrate into non-dividing cells (Lewis et al., EMBO J. (1992) 11: 3053-3058; Bukrinsky et al., Nature (1993) 365: 666-669; Gallay et al., Proc. Natl. Acad. Sci USA (1997) 94: 9825-9830; Gallay et al., Cell (1995) 80: 379-388; and Lewis et al., J. Virol. (1994) 68: 510). Replication-defective vectors from the human lentivirus human immunodeficiency virus (HIV) transduce target cells independent of mitosis (Naldini et al., Science (1996) 272: 263-267). The vectors proved highly efficient for in vivo gene delivery and achieved stable long-term expression of the transgene in several target tissues, such as the brain (Naldini et al., PNAS (1996) 93: 11382-1138; and Blomer et al., J. Virol. (1997) 71: 66416649), the retina (Miyoshi et al., PNAS (1997) 94: 10319-10323), the liver and the muscle (Kafri et al., Nature Genetics (1997) 17: 314-317).

A typical lentivirus is HIV, the etiologic agent of AIDS. In vivo, HIV can infect terminally differentiated cells that rarely divide, such as lymphocytes and macrophages. In vitro, HIV can infect primary cultures of monocyte-derived macrophages (MDM) as well as HeLa-Cd4 or T lymphoid cells arrested in the cell cycle by treatment with aphidicolin or y irradiation.

The complexity of the lentiviral genome may be exploited to build novel biosafety features in the design of a retroviral vector. In addition to the structural gag, pot and env genes common to all retroviruses, HIV contains two regulatory genes, tat and rev, essential for viral replication, and four accessory genes, vif vpr, vpu and nef that are not crucial for viral growth in vitro but are critical for in vivo replication and pathogenesis (Luciw., in Fields et al. (ed.), "Fields Virology", 3rd ed., (1996) p. 1881-1975 Lippincott-Raven Publishers, Philadelphia.).

The Tat and Rev proteins regulate the levels of HIV gene expression at transcriptional and post-transcriptional levels, respectively. Due to the weak basal transcriptional activity of the HIV LTR, expression of the provirus initially results in small amounts of multiply spliced transcripts coding for the Tat, Rev and Nef proteins. Tat dramatically increases HIV transcription by binding to a stem-loop structure (TAR) in the nascent RNA thereby recruiting a cyclin-kinase complex that stimulates transcriptional elongation by the polymerase II complex (Wei et alt, Cell (1998) 92: 451-462)). Once Rev reaches a threshold concentration, Rev promotes the cytoplasmic accumulation of unspliced and singly-spliced viral transcripts leading to the production of the late viral proteins.

Rev accomplishes that effect by serving as a connector between an RNA motif (the Rev-responsive element, RRE) found in the envelope coding region of the HIV transcript and components of the cell nuclear export machinery. Only in the presence of Tat and Rev are the HIV structural genes expressed and new viral particles produced (Luciw, supra).

In a first generation of HIV-derived vectors (Naldini et al., Science, supra), viral particles were generated by expressing the HIV-1 core proteins, enzymes and accessory factors from heterologous transcriptional signals and the envelope of another virus, most often the G protein of the vesicular stomatitis virus (VSV.G; Burns et al., PNAS (1993) 90: 8033-8037) from a separate plasmid.

In a second version of the system, the HIV-derived packaging component was reduced to the gag pol, tat and rev genes of HIV-1 (Zufferey et al., Nat. Biotech. (1997) 15: 871-875).

In either case, the vector itself carried the HIV-derived cis-acting sequences necessary for transcription, encapsidation, reverse transcription and integration (Aldovini & Young., J. Virol. (1990) 64: 1920-1926, Berkowitz et al., Virology (1995) 212: 718-723., Kaye et al., J. Virol. (1995) 69: 6588-6592; Lever et al., J. Virol. (1994) 63: 4085-4087; McBride et al., J. Virol. (1989) 70: 2963-2973; McBride et al., 3. Virol. (1997) 71: 4544-4554; Naldini et al., Science (supra); and Parolin et al., 3. Virol. (1994) 68: 3888-3895).

Such a vector thus encompassed from the 5' to 3' end, the HIV 5' LTR, the leader sequence and the 5' splice donor site, approximately 360 base pairs of the gag gene (with the gag reading frame closed by a synthetic stop codon), 700 base pairs of the env gene containing the RRE and a splice acceptor site, an internal promoter, for example, typically the immediate early enhancer/promoter of human cytomegalovirus (CMV) or that of the phosphoglycerokinase gene (PGK), the transgene and the HIV 3' LTR. Vector particles are produced by co-transfection of the constructs in 293T cells (Naldini et al. Science, supra). In that design, significant levels of transcription from the vector LTR and of accumulation of unspliced genomic RNA occur only in the presence of Tat and Rev.

Infection of cells is dependent on the active nuclear import of HIV preintegration complexes through the nuclear pores of the target cells. That occurs by the interaction of multiple, partly redundant, molecular determinants in the complex with the nuclear import machinery of the target cell. Identified determinants include a functional nuclear localization signal (NLS) in the gag matrix (MA) protein, the karyophilic virion-associated protein, vpr, and a C-terminal phosphotyrosine residue in the gag MA protein.

SUMMARY OF THE INVENTION

Accordingly, the instant invention relates to novel disarmed lentiviral vectors, such as packaging and transfer vectors, that direct the synthesis of both lentiviral vector transcripts which can be packaged and lentiviral proteins for rapid production of high titer recombinant lentivirus in mammalian cells. The results are infectious particles for delivering a foreign gene of interest to a target cell. The invention also provides cell lines for virus production.

DETAILED DESCRIPTION OF THE INVENTION

Figure 1:
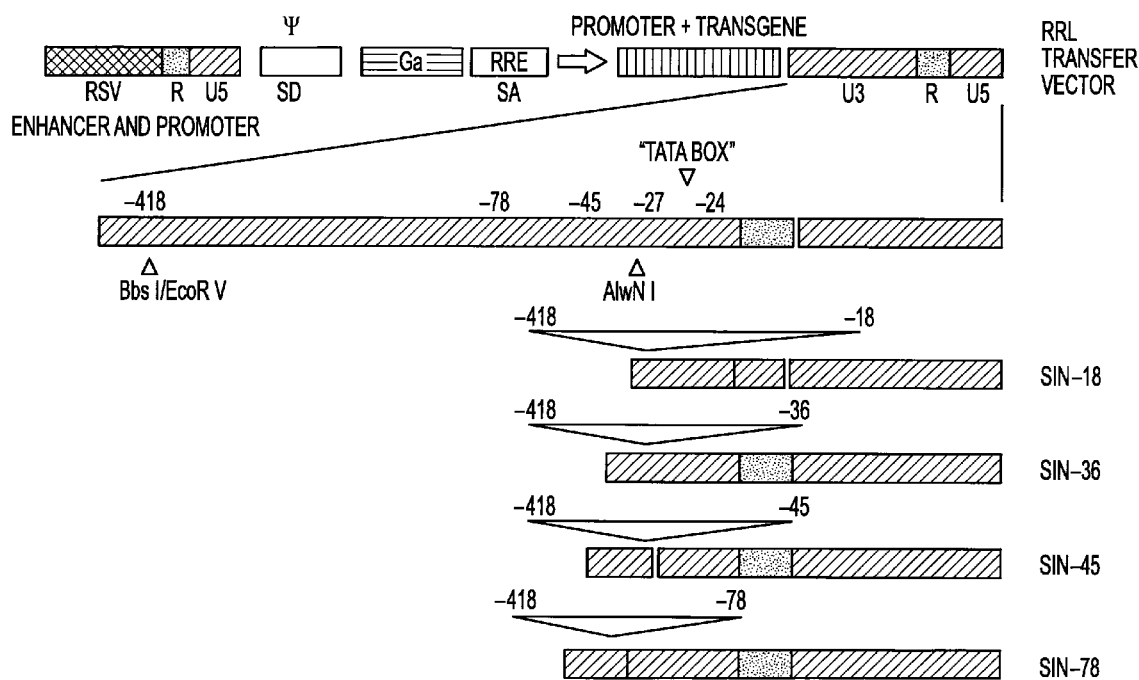
FIG. 1 depicts various lentivirus vectors. RSV is the Rous sarcoma virus enhancer/promoter; R is the R region of the LTR; U5 is the U5 region of the LTR; SD is a slice donor site, such as the HIV 5' major splice donor site; ψ is the Psi encapsidation signal sequence; Ga is a part of the gag gene; RRE is the rev responsive element; SA is a splice acceptor sequence; and U3 is the U3 region of the LTR.

The instant invention provides a recombinant lentivirus capable of infecting non-dividing cells as well as methods and means for making same. The virus is useful for the in vivo and ex vivo transfer and expression of nucleic acid sequences.

The lentiviral genome and the proviral DNA have the three genes found in retroviruses: gag, pol and env, which are flanked by two LTR sequences. The gag gene encodes the internal structural (matrix, capsid and nucleocapsid) proteins; the pot gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

The invention provides a method of producing a recombinant lentivirus capable of infecting a non-dividing cell comprising transfecting a suitable host cell with two or more vectors carrying the packaging functions, namely gag, pol and env, as well as rev and tat. As wilt be disclosed hereinbelow, vectors tacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

A lentiviral vector described herein may be packaged by three non-overlapping expression constructs, two expressing HIV proteins and the other the envelope of a different virus. Moreover, all HIV sequences known to be required for encapsidation and reverse transcription (Lever et al., supra, Aldovini & Young, supra; Kaye et al., supra; McBride & Panganiban, supra; McBride et al., supra; Parolin et al., supra; and Luciw, supra) are absent from the constructs, with the exception of the portion of the gag gene that contributes to the stem-loop structure of the HIV-1 packaging motif (McBride et al., supra).

A second strategy to improve vector biosafety takes advantage of the complexity of the lentiviral genome. The minimal set of HIV-1 genes required to generate an efficient vector was identified and all the other HIV reading frames were eliminated from the system. As the products of the removed genes are important for the completion of the virus life cycle and for pathogenesis, no recombinant can acquire the pathogenetic features of the parental virus. All four accessory genes of HIV could be deleted from the packaging construct without compromising gene transduction (Zufferey et al., supra).

The tat gene is crucial for HIV replication. The tat gene product is one of the most powerful transcriptional activators known and plays a pivotal role in the exceedingly high replication rates that characterize HIV-induced disease (Haynes et al., Science (1996) 271: 324-328; Ho et al., Nature (1995) 373:123-126; and lei et al., Nature (1995) 373 117-122).

The trans-acting function of Tat becomes dispensable if part of the upstream LTR in the vector construct is replaced by constitutively active promoter sequences. Furthermore, the expression of rev in trans allows the production of high-titer HIV-derived vector stocks from a packaging construct which contains only gag/pol. That design makes the expression of the packaging functions conditional on complementation available only in producer cells. The resulting gene delivery system, which conserves only three of the nine genes of HIV-1 and relies on four separate transcriptional units for the production of transducing particles, offers significant advantages in biosafety.

Tat is required in producer cells to generate vector of efficient transducing activity. However, that requirement can be offset by inducing constitutive high-level expression of vector RNA. Due to the low basal transcription from the HIV LTR, Tat is necessary to increase the abundance of vector transcripts and to allow for efficient encapsidation by the vector particles. When made in the absence of Tat, vector particles have ten-fold to twenty-fold reduced transducing activity. However, when strong constitutive promoters replace the HIV sequence in the 5' LTR of the transfer construct, vectors made without Tat exhibit a less than two-fold reduction in transducing activity. As Tat strongly upregulated transcription from the chimeric LTR, the transducing activity of the output particles must reach saturation. The abundance of vector RNA in producer cells thus appears to be a rate-limiting factor for transduction until a threshold is achieved. Conceivably, an upper limit is set by the total output of particles available to encapsidate vector RNA.

Successful deletion of the tat gene was unexpected in view of a reported additional role for Tat in reverse transcription (Harrich et al., EMBO J. (1997) 16; 1224-1235; and Huang et al., EMBO J. (1994) 13; 2886-2896). But the transduction pathway of the lentiviral vector mimics only in part the infection pathway of HIV. The vector is pseudotyped by the envelope of an unrelated virus and only contains the core proteins of HIV without any accessory gene product. The VSV envelope targets the vector to the endocytic pathway and it has been shown that redirection of HIV-1 from the normal route of entry by fusion at the plasma membrane significantly changes the biology of the infection. For example, Nef and cyclophilin A are required for the optimal infectivity of wild-type HIV-1 but not of a (VSV.G) HIV pseudotype (Aiken J. Virol. (1997) 71: 5871-5877). Also, the kinetics of reverse transcription may be more critical for the establishment of viral infection than for gene transduction, given the differences fin size and sequence between the virus and vector genome.

Also, the Rev dependence of gag-pot expression and of the accumulation of unspliced, packageable transcripts was exploited. Yu et al. [J. Virol. (1996) 70; 4530-4537] previously showed that the dependence on Rev can be used to make expression of HIV genes inducible. A core packaging system split in two separate non-overlapping expression constructs, one for the gag-pol reading frames optimized for Rev-dependent expression and the other for the Rev cDNA, therefore can be employed. Such a packaging system matches the performance of predecessors in terms of both yield and transducing efficiency. However, it increases significantly the predicted biosafety of the vector.

It has been suggested that the Rev-RRE axis could be replaced by the use of constitutive RNA transport elements of other viruses, although perhaps at the price of decreased efficiency (Srinivasakumar et al., J. Virol. (1997) 71; 5841-5848 and Corbeau et al., Gene Ther. (1998) 5: 99-104). Maintaining the Rev-dependence of the system allows for an additional level of biosafety through the splitting of the HIV-derived components of the packaging system.

The vectors per se, outside of the newly constructed vectors disclosed herein, are known in the art, see Naldini et al., Science, supra; and Zufferey et al. Generally the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest.

According to the above-indicated configuration of vectors and foreign genes, a vector can provide a nucleic acid encoding a viral envelope (env) gene. The env gene can be derived from any virus, including retroviruses. The env preferably is an amphotropic envelope protein which allows transduction of cells of human and other species.

It may be desirable to target the recombinant virus by linkage of the envelope protein with an antibody or a particular ligand for targeting to a receptor of a particular cell type. By inserting a sequence (including a regulatory region) of interest into the viral vector, along with another gene which encodes the ligand for a receptor on a specific target cell, for example, the vector is now target-specific. Retroviral vectors can be made target-specific by inserting, for example, a glycolipid or a protein. Targeting often is accomplished by using an antigen-binding portion of an antibody or a recombinant antibody-type molecule, such as a single chain antibody, to target the retroviral vector. Those of skill in the art will know of, or can readily ascertain without undue experimentation, specific methods to achieve delivery of a retroviral vector to a specific target.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV).

Other env genes such as vesicular stomatitis virus (VSV) protein G (VSV G), that of hepatitis viruses and of influenza also can be used.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegatovirus enhancer or the vaccinia P7.5 promoter. In some cases, such as the Moloney murine leukemia virus promoter-enhancer element, the promoter-enhancer elements are located within or adjacent to the LTR-sequences.

Preferably, the regulatory sequence is one which is not endogenous to the lentivirus from which the vector is being constructed. Thus, if the vector is being made from SIV, the SIV regulatory sequence found in the SIV LTR would be replaced by a regulatory element which does not originate from SIV.

While VSV C protein is a desirable env gene because VSV G confers broad host range on the recombinant virus, VSV G can be deleterious to the host cell. Thus, when a gene such as that for VSV G is used, it is preferred to employ an inducible promoter system so that VSV G expression can be regulated to minimize host toxicity when VSV C is expression is not required.

For example, the tetracycline-regulatable gene expression system of Gossen & Bujard (Proc. Natl. Acad. Sci. (1992) 89:5547-5551) can be employed to provide for inducible expression of VSV G when tetracycline is withdrawn from the transferred cell. Thus, the tet/VP16 transactivator is present on a first vector and the VSV C coding sequence is cloned downstream from a promoter controlled by tet operator sequences on another vector.

Such a hybrid promoter can be inserted in place of the 3' U3 region of the LTR of a transfer vector. As a result of transduction of target cells by the vector particles produced by the use of such a transfer vector, the hybrid promoter will be copied to the 5' U3 region on reverse transcription. In the target cells, such a conditional expression of a gene can be activated to express full-length packagable vector transcripts only in the presence of tTA—for example, after transduction of an appropriate packaging cell line expressing tTA.

Use of such vectors in producer cells allows one to "turn on" the production of the packagable vector mRNA messages at high levels only when needed. In contrast, on transduction of cells which do not express tTA, the hybrid promoter becomes transcriptionally silent. Such transcriptional silence was maintained even in the presence of HIV Tat protein, which is known to be capable of upregulating basal transcriptional activity of heterologous promoters. The promoter system significantly reduces the chance of mobilization of the vector genome even if transduced cells are infected by wild type HIV-1.

Another embodiment relates to a retroviral vector system based on lentivirus in which sequence homology (sequence overlap) between coding sequences of packaging and transfer vector constructs is eliminated. Importantly, vector particles produced by the use of such constructs retain high levels of transduction potential. Use of such constructs in a vector production system is expected to most significantly decrease the frequency of recombination events, which is a significant advance in biosafety associated with such a vector system.

It is known that throughout the gag-pol coding mRNA, several cis-acting repression sequences (CRS) are present. The sequences prevent transport of mRNA's to the cell cytoplasm and therefore prevent encoded protein expression. To suppress the action of CRS, HIV-1 mRNA's contain an antirepression signal called RRE to which Rev protein may bind. HIV-1 mRNA-Rev complexes then are efficiently transported to the cell cytoplasm where the complex dissociates and mRNA becomes available for translation.

At least two approaches are available for choosing the minimal amounts of HIV sequences necessary in Gag and Gag-Pol expressing packaging vectors. First, only the gag-pot gene could be inserted. In that case, all, or at least most of the CRS will need to be identified and mutated without effecting the encoded amino acid sequence. If that is accomplished, the Rev gene can be eliminated from the vector system.

Second, the minimal RRE element can be introduced to the gag-pol expression cassette so that the sequence thereof will be part of the resulting mRNA. In that case, expression of Gag and Gag-Pol polyproteins will require presence of the antirepressor, Rev. Rev protein itself, however, does not need to be part of the gag-pot expression vector but could be provided in trans from independent and, preferably, nonoverlapping with the gag-pol expression cassette.

In the system where Rev protein is not required for efficient production of transfer vector mRNA, the rev gene and RRE element may be eliminated from the vector system as a further biosafety measure. In such a system, however, if the gag-pol gene in whole or in part is transferred into a vector recipient as the result of a homologous or a non-homologous recombination event the expression may occur.

In contrast, a vector system in which gag-pol gene expression is dependent on Rev may be a valuable safety alternative. Thus, if a Rev utilizing vector system is designed so all of the components do not have homologous sequences, in the unlikely event of recombination, which would result in transfer the of gag-pol sequences to the vector recipient, the expression thereof is much less likely to occur since the transferred recombinant must contain both the RRE element as well as Rev coding sequence capable of being expressed.

Suitable vectors are the type-7 vectors which in comparison to type-2 vectors, integrate further modification of HIV-1 sequences: one base mutation within the SD site to prevent splicing of full length mRNA; absence of the HIV-1 SA site and flanking sequences; contains only 43 bases of 5' gag ORF; and absence of the RRE element. The type-7 vectors encompass only 43 bases homologous to pMDLg/pRRE and no homology to pMDLg/pRRE. 2 and pMDLg/pRRE. 3 packaging vectors. Table 1 below provides an example of vector titer yields obtained by transfection of the described minimally overlapping and nonoverlapping constructs.

TABLE 1

| Packaging Vector (12 µg of plasmid DNA transfected) | Transfer vector (10 µg of plasmid DNA transfected) | Rev expressing Plasmid (2.5 µg of plasmid DNA transfected) | VSV/G expressing plasmid (3.5 µg of plasmid DNA transfected) | Titer (Transducing Units per 1 ml of supernatant) |
|---|---|---|---|---|
| pMDLg/pRRE | pCCL7sinCMVGFPpre | PRSV-Rev | pMD.G | $4.71 \times 10^6$ |
| pMDLg/pRRE.2 | pCCL7sinCMVGFPpre | pRSV-Rev | pMD.G | $2.74 \times 10^6$ |
| pMDLg/pRRE.3 | pCCL7sinCMVGFPpre | pRSV-Rev | pMD.G | $1.16 \times 10^6$ |

As the main property of interest for HIV-derived vectors is the ability to transduce nondividing and slowly dividing cells and tissues, nonoverlapping vectors were tested for transduction in cell cycle arrested cells. In contrast to MoMLV vectors, minimal HIV-derived vectors maintained transduction potential in both dividing and growth arrested cells.

Furthermore, an HIV-1 RNA element present in the packaging vector gag-pol mRNA was observed to lead to specific encapsidation of significant amounts of the message into released vector particles under certain conditions. The element serves as the HIV-1 major splice donor site (SD) and consists of at least nucleotides, GACUGGUGAG (SEQ ID NO: 1). In the absence of transfer vector expression, vector particles generated only by pMDLg/pRRE packaging construct have no detectable gag-pol RNA message. Analysis of total RNA extracted from the cells which produced the vector particles, showed that expression levels in all cases were similar. When 5'mRNA regions of the tested packaging vectors were compared, it became apparent that the specified above sequence is the determinant which provides specific encapsidation of the messages.

The heterologous or foreign nucleic acid sequence, the transgene, is linked operably to a regulatory nucleic acid sequence. As used herein, the term "heterologous" nucleic acid sequence refers to a sequence that originates from a foreign species, or, if from the same species, it may be substantially modified from the original form. Alternatively, an unchanged nucleic acid sequence that is not expressed normally in a cell is a heterologous nucleic acid sequence.

The term "operably linked" refers to functional linkage between a regulatory sequence and a heterologous nucleic acid sequence resulting in expression of the latter. Preferably, the heterologous sequence is linked to a promoter, resulting in a chimeric gene. The heterologous nucleic acid sequence is preferably under control of either the viral LTR promoter-enhancer signals or of an internal promoter, and retained signals within the retroviral LTR can still bring about efficient expression of the transgene.

The foreign gene can be any nucleic acid of interest which can be transcribed. Generally, the foreign gene encodes a polypeptide. Preferably the polypeptide has some therapeutic benefit. The polypeptide may supplement deficient or nonexistent expression of an endogenous protein in a host cell. The polypeptide can confer new properties on the host cell, such as a chimeric signaling receptor, see U.S. Pat. No. 5,359,046. The artisan can determine the appropriateness of a foreign gene practicing techniques taught herein and known in the art. For example, the artisan would know whether a foreign gene is of a suitable size for encapsidation and whether the foreign gene product is expressed properly.

It may be desirable to modulate the expression of a gene regulating molecule in a cell by the introduction of a molecule by the method of the invention. The term "modulate" envisions the suppression of expression of a gene when it is over-expressed or augmentation of expression when it is under-expressed. Where a cell proliferative disorder is associated with the expression of a gene, nucleic acid sequences that interfere with the expression of a gene at the translational level can be used. The approach can utilize, for example, antisense nucleic acid, ribozymes or triplex agents to block transcription or translation of a specific mRNA, either by masking that mRNA with an antisense nucleic acid or triplex agent, or by cleaving same with a ribozyme.

Antisense nucleic acids are DNA or RNA molecules which are complementary to at least a portion of a specific mRNA molecule (Weintraub, Sci. Am. (1990) 262: 40). In the cell, the antisense nucleic acids hybridize to the corresponding mRNA forming a doublestranded molecule. The antisense nucleic acids interfere with the translation of the mRNA since the cell will not translate a mRNA that is doublestranded. Antisense oligomers of about 16 nucleotides or more are preferred since such are synthesized easily and are less likely to cause problems than larger molecules when introduced into the target cell. The use of antisense methods to inhibit the in vitro translation of genes is well known in the art (Marcus-Sakura, Anal. Biochem. (1988) 172: 289).

The antisense nucleic acid can be used to block expression of a mutant protein or a dominantly active gene product, such as amyloid precursor protein that accumulates in Alzheimer's disease. Such methods are also useful for the treatment of Huntington's disease, hereditary Parkinsonism and other diseases. Antisense nucleic acids are also useful for the inhibition of expression of proteins associated with toxicity.

Use of an oligonucleotide to stall transcription can be by the mechanism known as the triplex strategy since the oligomer winds around double-helical DNA, forming a three-strand helix. Therefore, the triplex compounds can be designed to recognize a unique site on a chosen gene (Maher et al., Antisense Res and Dev. (1991) 1 (3): 227; Helene., Anticancer Drug Dis. (1991) 6 (6): 569).

Ribozymes are RNA molecules possessing the ability to specifically cleave other single-stranded RNA in a manner analogous to DNA restriction endonucleases. Through the modification of nucleotide sequences which encode those RNA's, it is possible to engineer molecules that recognize and cleave specific nucleotide sequences in an RNA molecule (Cech, J. Amer. Med Assn. (1988) 260: 3030). A major advantage of that approach is only mRNA's with particular sequences are inactivated.

It may be desirable to transfer a nucleic acid encoding a biological response modifier. Included in that category are immunopotentiating agents including nucleic acids encoding a number of the cytokines classified as "interleukins", for example, interleukins 1 through 12. Also included in that category, although not necessarily working according to the same mechanism, are interferons, and in particular gamma interferon (y-IFN), tumor necrosis factor (TNF) and granulocyte-macrophage-colony stimulating factor (GM-CSF). It may be desirable to deliver such nucleic acids to bone marrow cells or macrophages to treat inborn enzymatic deficiencies or immune defects. Nucleic acids encoding growth factors, toxic peptides, ligands, receptors or other physiologically important proteins also can be introduced into specific non-dividing cells.

Thus, the recombinant lentivirus of the invention can be used to treat an HIV-infected cell (e.g. T-cell or macrophage) with an anti-HIV molecule. In addition, respiratory epithelium, for example, can be infected with a recombinant lentivirus of the invention having a gene for cystic fibrosis transmembrane conductance regulator (CFTR) for treatment of cystic fibrosis.

The method of the invention may also be useful for neuronal, glial, fibroblast or mesenchymal cell transplantation, or "grafting", which involves transplantation of cells infected with the recombinant lentivirus of the invention ex vivo, or infection in vivo into the central nervous system or into the ventricular cavities or subdurally onto the surface of a host brain. Such methods for grafting will be known to those skilled in the art and are described in Neural Grafting in the Mammalian CNS, Bjorklund & Stenevi, eds. (1985).

For diseases due to deficiency of a protein product, gene transfer could introduce a normal gene into the affected tissues for replacement therapy, as well as to create animal models for the disease using antisense mutations. For example, it may be desirable to insert a Factor VIII or IX encoding nucleic acid into a lentivirus for infection of a muscle, spleen or liver cell.

The promoter sequence may be homologous or heterologous to the desired gene sequence. A wide range of promoters may be utilized, including a viral or a mammalian promoter. Cell or tissue specific promoters can be utilized to target expression of gene sequences in specific cell populations. Suitable mammalian and viral promoters for the instant invention are available in the art. A suitable promoter is one which is inducible or conditional.

Optionally during the cloning stage, the nucleic acid construct referred to as the transfer vector, having the packaging signal and the heterologous cloning site, also contains a selectable marker gene. Marker genes are utilized to assay for the presence of the vector, and thus, to confirm infection and integration. The presence of a marker gene ensures the selection and growth of only those host cells which express the inserts. Typical selection genes encode proteins that confer resistance to antibiotics and other toxic substances e.g. histidinol, puromycin, hygromycin, neomycin, methotrexate etc. and cell surface markers.

The recombinant virus of the invention is capable of transferring a nucleic acid sequence into a mammalian cell. The term, "nucleic acid sequence", refers to any nucleic acid molecule, preferably DNA, as discussed in detail herein. The nucleic acid molecule may be derived from a variety of sources, including DNA, cDNA, synthetic DNA, RNA or combinations thereof. Such nucleic acid sequences may comprise genomic DNA which may or may not include naturally occurring introns. Moreover, such genomic DNA may be obtained in association with promoter regions, poly A sequences or other associated sequences. Genomic DNA may be extracted and purified from suitable cells by means well known in the art. Alternatively, messenger RNA (mRNA) can be isolated from cells and used to produce cDNA by reverse transcription or other means.

Preferably, the recombinant lentivirus produced by the method of the invention is a derivative of human immunodeficiency virus (HIV). The env will be derived from a virus other than HIV.

The method of the invention provides, in some embodiments, three vectors which provide all of the functions required for packaging of recombinant virions, such as, gag, pot, env, tat and rev, as discussed above. As noted herein, tat may be deleted functionally for unexpected benefits. There is no limitation on the number of vectors which are utilized so long as the vectors are used to transform and to produce the packaging cell line to yield recombinant lentivirus.

The vectors are introduced via transfection or infection into the packaging cell line. The packaging cell line produces viral particles that contain the vector genome. Methods for transfection or infection are well known by those of skill in the art. After co-transfection of the packaging vectors and the transfer vector to the packaging cell line, the recombinant virus is recovered from the culture media and titered by standard methods used by those of skill in the art.

Thus, the packaging constructs can be introduced into human cell lines by calcium phosphate transfection, lipofection, electroporation or other method, generally together with a dominant selectable marker, such as neo, DHFR, Gln synthetase or ADA, followed by selection in the presence of the appropriate drug and isolation of clones. The selectable marker gene can be linked physically to the packaging genes in the construct.

Stable cell lines wherein the packaging functions are configured to be expressed by a suitable packaging cell are known. For example, see U.S. Pat. No. 5,686,279; and Ory et al., Proc. Natl. Acad. Sci. (1996) 93: 11400-11406, which describe packaging cells.

Zufferey et al. supra, teach a lentiviral packaging plasmid wherein sequences 3' of pot including the HIV-1 env gene are deleted. The construct contains tat and rev sequences and the 3' LTR is replaced with poly A sequences. The 5' LTR and psi sequences are replaced by another promoter, such as one which is inducible. For example, a CMV promoter or derivative thereof can be used.

The packaging vectors of interest contain additional changes to the packaging functions to enhance lentiviral protein expression and to enhance safety. For example, all of the HIV sequences upstream of gag can be removed. Also, sequences downstream of env can be removed. Moreover, steps can be taken to modify the vector to enhance the splicing and translation of the RNA.

To provide a vector with an even more remote possibility of generating replication competent lentivirus, the instant invention provides for lentivirus packaging plasmids wherein tat sequences, a regulating protein which promotes viral expression through a transcriptional mechanism, are deleted functionally. Thus, the tat gene can be deleted, in part or in whole, or various point mutations or other mutations can be made to the tat sequence to render the gene nonfunctional. An artisan can practice known techniques to render the tat gene nonfunctional.

The techniques used to construct vectors, and to transfect and to infect cells, are practiced widely in the art. Practitioners are familiar with the standard resource materials which describe specific conditions and procedures. However, for convenience, the following paragraphs may serve as a guideline.

Construction of the vectors of the invention employs standard ligation and restriction techniques which are well understood in the art (see Maniatis et al., in Molecular Cloning: A Laboratory Manual, Cold Spring Harbor Laboratory, N.Y., 1982). Isolated plasmids, DNA sequences or synthesized oligonucleotides are cleaved, tailored and religated in the form desired.

Site-specific DNA cleavage is performed by treating with the suitable restriction enzyme (or enzymes) under conditions which are understood in the art, and the particulars of which are specified by the manufacturer of the commercially available restriction enzymes, see, e.g. New England Biolabs, Product Catalog. In general, about 1 µg of plasmid or DNA sequences is cleaved by one unit of enzyme in about 20 µl of buffer solution. Typically, an excess of restriction enzyme is used to ensure complete digestion of the DNA substrate. Incubation times of about one hour to two hours at about 37° C. are workable, although variations can be tolerated. After each incubation, protein is removed by extraction with phenol/chloroform, which may be followed by ether extraction, and the nucleic acid recovered from aqueous fractions by precipitation with ethanol. If desired, size separation of the cleaved fragments may be performed by polyacrylamide gel or agarose gel electrophoresis using standard techniques. A general description of size separations is found in Methods of Enzymology 65: 499560 (1980).

Restriction cleaved fragments may be blunt ended by treating with the large fragment of $E.\ coli$ DNA polymerase I (Klenow) in the presence of the four deoxynucleotide triphosphates (dNTP's) using incubation times of about 15 to 25 minutes at 20 ad in 50 mM Tris (pH 7.6) 50 mM NaCl, 6 mM $MgCl_2$, 6 mM DTT and 5-10 µM dNTP's. The Klenow fragment fills in at 5' sticky ends but chews back protruding 3' single strands, even though the four dNTP's are present. If desired, selective repair can be performed by supplying only one of the dNTP's, or with selected dNTP's, within the limitations dictated by the nature of the sticky ends. After treatment with Klenow, the mixture is extracted with phenol/chloroform and ethanol precipitated. Treatment under appropriate conditions with SI nuclease or Bal-31 results in hydrolysis of any single-stranded portion.

Ligations can be performed in 15-50 µl volumes under the following standard conditions and temperatures: 20 mM Tris-Cl pH 7.5, 10 mM $MgCl_2$, 10 mM DTT, 33 mg/ml BSA, 10 mM-50 mM NaCl and either 40 µM ATP, 0.01-0.02 (Weiss) units T4 DNA ligase at 0'-C (for "sticky end" ligation) or 1 mM ATP, 0.3-0.6 (Weiss) units T4 DNA ligase at 14 CG (for "blunt end" ligation). Intermolecular "sticky end" ligations are usually performed at 33-100 µg/ml total DNA concentrations (5-100 mM total end concentration). Intermolecular blunt end ligations (usually employing a 10-30 fold molar excess of linkers) are performed at 1 µM total ends concentration.

Thus, according to the instant invention, a lentiviral packaging vector is made to contain a promoter and other optional or requisite regulatory sequences as determined by the artisan, gag, pol, rev, env or a combination thereof, and with specific functional or actual excision of tat, and optionally other lentiviral accessory genes.

Lentiviral transfer vectors (Naldini et al., Science supra; Proc. Natl. Acad. Sci., supra) have been used to infect human cells growth-arrested in vitro and to transduce neurons after direct injection into the brain of adult rats. The vector was efficient at transferring marker genes in vivo into the neurons and long term expression in the absence of detectable pathology was achieved. Animals analyzed ten months after a single injection of the vector, the longest time tested so far, showed no decrease in the average level of transgene expression and no sign of tissue pathology or immune reaction. (Blomer et al., supra). An improved version of the lentiviral vector in which the HIV virulence genes env, vif, vpr, vpu and nef were deleted without compromising the ability of the vector to transduce non-dividing cells have been developed. The multiply attenuated version represents a substantial improvement in the biosafety of the vector (Zufferey et al., supra).

In transduced cells, the integrated lentiviral vector generally has an LTR at each termini. The 5' LTR may cause accumulation of "viral" transcripts that may be the substrate of recombination, in particular in HIV-infected cells. The 3' LTR may promote downstream transcription with the consequent risk of activating a cellular protooncogene.

The U3 sequences comprise the majority of the HIV LTR. The U3 region contains the enhancer and promoter elements that modulate basal and induced expression of the HIV genome in infected cells and in response to cell activation, Several of the promoter elements are essential for viral replication. Some of the enhancer elements are highly conserved among viral isolates and have been implicated as critical virulence factors in viral pathogenesis. The enhancer elements may act to influence replication rates in the different cellular target of the virus (Marthas et al. J. Virol. (1993) 67: 6047-6055).

As viral transcription starts at the 3' end of the U3 region of the 5' LTR, those sequences are not part of the viral mRNA and a copy thereof from the 3' LTR acts as template for the generation of both LTR's in the integrated provirus. If the 3' copy of the U3 region is altered in a retroviral vector construct, the vector RNA still is produced from the intact 5' LTR in producer cells, but cannot be regenerated in target cells. Transduction of such a vector results in the inactivation of both LTR's in the progeny virus. Thus the retrovirus is self-inactivating (SIN) and those vectors are known as Sin transfer vectors.

There are, however, limits to the extent of the deletion at the 3' LTR. First, the 5' end of the U3 region serves another essential function in vector transfer, being required for integration (terminal dinucleotide+att sequence). Thus, the terminal dinucleotide and the att sequence may represent the 5' boundary of the U3 sequences which can be deleted. In addition, some loosely defined regions may influence the activity of the downstream polyadenylation site in the R region. Excessive deletion of U3 sequence from the 3' LTR may decrease polyadenylation of vector transcripts with adverse consequences both on the titer of the vector in producer cells and the transgene expression in target cells. On the other hand, limited deletions may not abrogate the transcriptional activity of the LTR in transduced cells.

New versions of a lentivirus transfer vector described herein carry increasing deletions of the U3 region of the 3' LTR (FIG. 1: the U3 deletions span from nucleotide-418 of the U3 LTR to the indicated position, SIN-78, SIN-45, SIN-36 and SIN-18). Lentiviral vectors with almost complete deletion of the U3 sequences from the 3' LTR were developed without compromising either the titer of vector in producer cells or transgene expression in target cells. The most extensive deletion (−418 to −18) extends as far as to the TATA box, therefore abrogating any transcriptional activity of the LTR in transduced cells. Thus, the lower limit of the 3S deletion may extend as far as including the TATA box. The deletion may be of the remainder of the U3 region up to the R region. That represents a dramatic gain in vector safety. The various deletions were produced practicing methods known in the art.

Surprisingly, the average expression level of the transgene was even higher in cells transduced by the SIN vectors as compared to more intact vectors. That was probably due to the removal of transcriptional interference from the upstream HIV LTR on the internal promoter. SIN-type vectors with such extensive deletions of the U3 region could not be generated for murine leukemia virus (MLV)-based retroviral vectors without compromising efficiency of transduction.

The 5' LTR of transfer vector construct was modified by substituting part or all of the transcriptional regulatory elements of the U3 region with heterologous enhancer/promoters. The changes were made to enhance the expression of transfer vector RNA in producer cells; to allow vector production in the absence of the HIV tat gene; and to remove the upstream wiid-type copy of the HIV LTR that can recombine with the 3'deleted version to "rescue" the above described SIN vectors.

Thus, vectors containing the above-described alterations at the 5' LTR, 5' vectors, can find use as transfer vectors because of the sequences to enhance expression and in combination with packaging cells that do not express tat.

Such 5' vectors can also carry modifications at the 3' LTR as discussed hereinabove to yield improved transfer vectors which have not only enhanced expression and can be used in packaging cells that do not express tat but can be self-inactivating as well.

The transcription from the HIV LTR is highly dependent on the transactivator function of the tat protein. In the presence of tat, often expressed by the core packaging construct existing in producer cells, vector transcription from the HIV LTR is stimulated strongly. As that full-length "viral" RNA has a full complement of packaging signals the RNA is encapsidated efficiently into vector particles and transferred to target cells. The amount of vector RNA available for packaging in producer cells is a rate-limiting step in the production of infectious vector.

Figure 2:
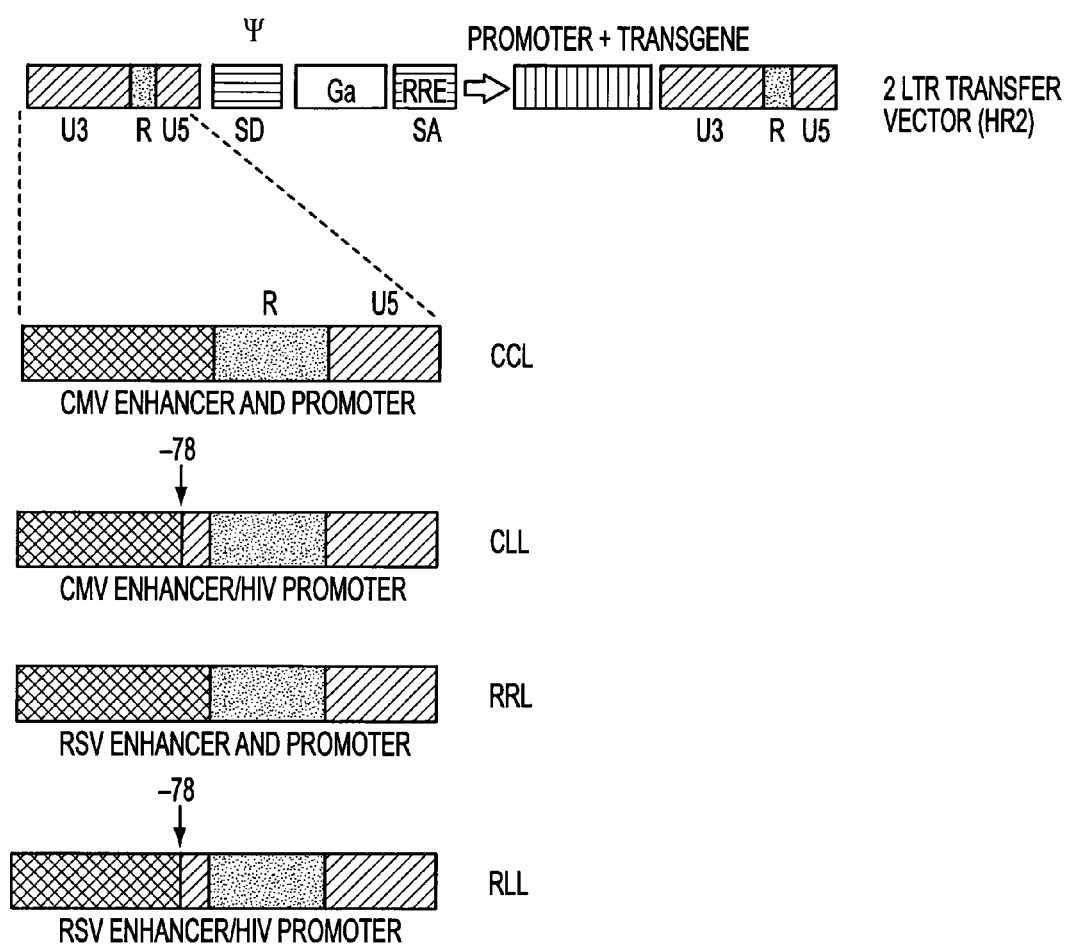
FIG. 2 depicts additional lentivirus vectors. CMV is cytomegalovirus. Otherwise the symbols are as found in the legend to FIG. 1.

The enhancer or the enhancer and promoter regions of the 5' LTR were substituted with the enhancer or the enhancer and promoter of the human cytomegalovirus (CMV) or Rous sarcoma virus (RSV), respectively, see FIG. 2 for a schematic of the constructs and the code names of the hybrid vectors. The CCL and RRL vectors have complete substitution of the 5' U3 region.

The control lentivector HR2 and the panel of 5' hybrids were compared in producer cells transfected with the transfer vector, and with or without packaging constructs, which provide the tat transactivator. The transcriptional level of the four chimeric vectors is higher than that of a control lentivector both in the presence and in the absence of the packaging construct. Alt chimeric vectors efficiently transfer the transgene into target cells and the RRL vector performs as well as the control HR2 vector. Finally, integration of the vector in target cells was confirmed by examining transduced cells at an early and a later passage after transduction. No decrease was observed in the percentage of transgene-positive cells indicating that the vector had been integrated.

The high level of expression of the 5' LTR modified transfer vector RNA obtained in producer cells in the absence of a packaging construct indicates the producing vector is functional in the absence of a functional tat gene. Functional deletion of the tat gene as indicated for the packaging plasmid disclosed hereinabove would confer a higher level of biosafety to the lentiviral vector system given the number of pathogenetic activities associated with the tat protein. Thus, a lentiviral vector of significantly improved biosafety is a SIN transfer vector that has no with d-type copy of the HIV LTR either at the 5' or at the 3' end, which is used in conjunction with tat-less packaging vectors as described herein.

Viral supernatants are harvested using standard techniques such as filtration of supernatants 48 hours post transfection. The viral titer is determined by infection of, for example, $10^6$ NIH 3T3 cells or $10^5$ HeLa cells with an appropriate amount of viral supernatant, in the presence of 8 µg/ml polybrene (Sigma Chemical Co., St. Louis, Mo.). Forty-eight hours later, the transduction efficiency is assayed.

Thus, the instant invention provides methods and means for producing high titer recombinant virus. Those virus particle preparations can be used to infect target cells using techniques known in the art. Thus the instant invention will find use in ex vivo gene therapy applications wherein target cells are removed from a host, transformed in culture practicing known techniques and then returned to the host.

The invention now having been described in detail, provided hereinbelow are non-limiting examples demonstrating various embodiments of the instant invention.

EXAMPLE 1

Construction of Lentiviral Packaging Plasmids

The lentiviral packaging plasmids were derived from the plasmid pCMVΔR8.9 (ΔVprΔVifΔVpuΔNef described previously in Zufferey et al., supra. All the remaining sequences of the nef gene in pCMVΔR8.9 were removed by digesting with XhoI and BstEII, filing in with Klenow and religating. The construction deleted 100 base pairs, joining the truncated env reading frame of HIV-1 to the genomic insulin polyadenylation site and yielding the plasmid pCMVΔR8.73.

In another embodiment of the invention, 133 base pairs of CMV-derived sequences downstream of the CMV promoter were deleted in the plasmid pCMVΔR8.73. That sequence contains a splice donor site and it was removed by digestion of the plasmid pCMVΔR8.73 with SacII and religation of the larger fragment, obtaining the plasmid pCMVΔR8.74.

In another embodiment of the invention, all the HIV-derived sequences remaining in the plasmid pCMVΔR8.74 upstream of the initiating codon of the gag gene were removed, except for the consensus 5' splice donor site. At the same time, the sequence upstream of the gag gene was changed for optimal translation efficiency obtaining the plasmid pCMVΔR8.75. pCMVΔR8.75 was derived from pCMVΔR8.74 by replacing the 94 bp SstII-ClaI at fragment with an SstII-ClaI oligonucleotide linker consisting of, 5'-GGGACTGGTGAGTGAATTCGAGATCTOCCGCCGCCATGGGTGCGAGAGCGTCAGTATTAAGCGGGGGAGAATTAGAT-3' (SEQ ID NO: 2) and 5'-CGATCTAATTCTCTCCCCCGCT-TAATACTGACGCTCTCGCACOCCATOG-GCGGCGGCAGATCTC GAATTCACTCACCAGTC-CCGC-3' (SEQ ID NO: 3).

In another embodiment of the invention, an inducible packaging construct was obtained by replacing the PstI-SacII fragment of pCMVΔR8.74 containing the CMV promoter with seven tandem copies of the tetracycline operator sequences linked to a minimal CMV promoter. The tet-regulated packaging plasmid pTet ΔR8.74 was obtained.

EXAMPLE 2

Construction of Lentiviral Transfer Vectors

The lentiviral transfer vector plasmids were derived from the plasmid pHR'-CMV-Lacz described previously in Naldini et al. Science, supra. pHR2 is a lentiviral transfer vector in which 124 bp of nef sequences upstream of the 3' LTR in pHR' were replaced with a polylinker both to reduce HIV1 sequences and to facilitate transgene cloning. pHR2 was derived from pHR'-CMV-LacZ by replacing the 4.6 kb ClaI-StuI fragment with the 828 bp ClaI-StuI fragment generated by PCR using pHR'-CMV-LacZ as the template and the oligonucleotide, 5'-CCATCGATCACGAGACT AGTC-CTACGTATCCCCGGGGACGGGATCCGCG-GAATTCCGTTTAAGAC-3' (SEQ ID NO: 4) and 5'-TTATAATGTCAAGGCCTCTC-3' (SEQ ID NO: 5) in a three-part ligation with a 4.4 kb StuI-NcoI fragment and a 4.5 kb NcoI-ClaI fragment from pHR'-CMV-LacZ.

In another embodiment of the invention, pHR3 is a lentiviral transfer vector in which 148 bp of env coding sequences (including an ATG) upstream of the Rev Response Element (RRE) in pHR2 were deleted. pHR3 was derived from pHR2 by replacing the 893 bp NotI-SpeI fragment of pHR2 with a 747 bp NotI-SpeI fragment generated by PCR using pHR2 as the template with oligonucleotide primers 5'-GCGGCCG-CAGGAGCTTTGTTCCTTGG-3' (SEQ ID NO: 6) and 5'-TACGTAGGACTAGTCTCG-3' (SEQ ID NO: 7).

In another embodiment of the invention, pHR5 is a lentiviral transfer vector in which 310 bp gag coding sequences (all gag coding sequences downstream from amino acid 15 of the Gag protein) were deleted from pHR2. pHR5 was derived by digestion of pHR2 with NruI, addition of a NotI linker (synthetic oligonucleotide 5'-TTGCGGCCGCAA-3'; SEQ ID NO: 8), digestion with NotI to excise the 310 bp fragment, followed by religation.

In another embodiment of the invention, pHR6 is a lentiviral vector in which the 5' splice donor signal was mutated (TGGT to TGAT) to enhance production of full-length transcripts capable of being packaged. pHR6 was derived from pHR5 by replacing the 239 bp AflII-ApoI fragment with a 239 bp AflII-ApoI fragment generated by PCR using a pHR2 as the template with oligonucleotide primers 5'-CCACTGCT-TAAGCCT-3' (SEQ ID NO: 9) and 5'-CAAATTTTTGGCG-TACTCATCAGTCGCCCCCCTCG-3-(SEQ ID NO: 10).

All PCR fragments were generated by first cloning the PCR reaction product directly into the TA cloning vector pCR2.1 (Invitrogen) followed by sequence verification and excision with the appropriate enzymes.

EXAMPLE 3

Construction of 5' LTR Chimeric Lentiviral Transfer Vectors

In another embodiment of the invention, the 5' LTR of the lentiviral vector contains the enhancer and promoter from the U3 region of the Rous Sarcoma Virus (RSV) joined to the R region of HIV-1 (plasmid pRRL). pRRL is a lentiviral transfer vector in which the enhancer and promoter (nucleotides −233 to −1 relative to the transcriptional start site) of RSV is precisely fused to the R region of HIV-1 using an oligonucleotide linker. pRRL was derived from plasmids pRT43.RSV.F3, see WO97/07225, and pHR2 by replacing the 3.4 kb EcoRI-HpaI fragment of pRT43.RSV.F3 with the 0.67 kb BglII-NotI fragment from pHR2 and the 1.7 kb NotI-StuI fragment from pHR2 along with a synthetic EcoRI-BglII oligonucleotide tinker consisting of oligonucleotides 5'-AATTGCCGOAT-TGCAGA GATATTGTATTTAAGTGCCTAGCTC-GATACAATAAACGGGTCTCTCTGGTTAGACCA-3' (SEQ ID NO: 11) and 5'-GATCTGGTCTAACCAGAGAGACCCGTT-TATTGTATCGAGCTA GGCACTTAAATA-CAATATCTCTGCAATGCGGC-3' (SEQ D NO: 12).

In another embodiment of the invention, the 5' LTR of the lentiviral vector contains the enhancer (nucleotides-233--50 relative to the transcriptional start site) of the Rous Sarcoma Virus (RSV) joined to the promoter region (from the position –78 bp relative to the transcriptional start site) of HIV-1 (plasmid pRLL).

pRLL is a lentiviral transfer vector in which the enhancer of RSV is fused to the promoter region of HIV-1 using an oligonucleotide linker. pRRL was derived from plasmids pRT43,RSV.F3 and pHR2 by replacing the 3.4 kb EcoRI-HpaI fragment of pRT43.RSV.FS with the 724 kb AlwNI-NotI fragment from pHR2 and the 1.7 kb NotI-StuI fragment from pHR2 along with a synthetic EcoRI-AlwNI oligonucleotide linker consisting of the oligo, 5'-AATTGGAGGCGTG-GCCTGGG CGGGACTGGGGAGTGGCGAGCCCTCA-GATC-3' (SEQ ID NO: 13) and the oligonucleotide, 5'-CTGAGGGCTCGCCACTCCCCAGTCCCGC-CCAGGCACGCCTCC-3' (SEQ ID NO; 14).

In another embodiment of the invention (plasmid pCCL), the 5' LTR of the lentiviral vector contains the immediate early enhancer and promoter (nucleotides –673 to –1, relative to the transcriptional start site according to Boshart et al. (Cell (1985) 41: 521-530), of human cytomegalovirus (CMV) joined to the R region of HIV-1. pCCL was derived from plasmids 5'-GATATGATCAGATC-3' (SEQ ID NO: 15) and 5'-CTGATCA-3' (SEQ ID NO: 16) and a three-part ligation along with a 54 kb AlwN-AvrII fragment and a 6.1 kb AvrII-BbsI fragment from pRRL.

pRRL.SIN-45 was derived from pRRL by replacing the 493 bp BbsI-AlwNI fragment in the 3' LTR with an oligonucleotide linker consisting of synthetic oligonucleotides, 5'-GATATGATCA GAGCCCTCAGATC-3' (SEQ ID NO: 17) and 5'-CTGAGGGCTCTGATCA-3' (SEQ ID NO: 18) in a three-part ligation along with a 54 kb AlwNI-AvrII fragment and a 6.1 kb AvrII-BbsI fragment from pRRL.

pRRL.SIN-78 was derived from pRRL by replacing the 493 bp BbsI-AlwNI fragment in the 3' LTR with an oligonucleotide linker consisting of, 5'-GATATGATCAGGAG-GCGTGGCCTGG GCGGGACTGGGGAGTGGCGAGC-CCTCAGATC-3' (SEQ ID NO: 19) and oligonucleotide 5'-CTGAGGGCTCGCCACTCCCCAGTCCCGC-CCAGGCCACGCCTCCTGATCA-3' (SEQ ID NO: 20) in a three-part ligation along with a 0.54 kb AlwNI-AvrII fragment and a 6.1 kb AvrII-BbsI fragment from pRRI.

EXAMPLE 5

Construction of Stable Lentiviral Packaging Cell)
0-28 and of Stable Producers of Lentiviral Vector The 293G cell line was used to generate stable lentiviral packaging cells. 293G cells express the tetR/VP16 transactivator from the MD cassette (CMV promoter and intervening sequences—exons 2 and 3, intron 2- and poly (A) site from the human B globin gene) and the VSV envelope from a minimal CMV promoter linked to a tandem repeat of seven tetracycline operator sites (tet). The expression of VSV G thus is regulated by the level of tetracycline in the culture medium, being suppressed in the presence of the antibiotic (Gossen & Bujard. Proc. Natl. Acad. Sci. USA (1992) 89: 5547-5551); and Ory et al., supra (1997). The 293G cells were maintained routinely in DMEM/low glucose culture medium supplemented with 10% donor calf serum and containing 1 µg/ml tetracycline. A 15 cm plate of 293G cells were transfected using lipofectamine (GIBCO BRL) with 13.36 µg of the packaging plasmid pCMVΔR8.74 and 1.33 µg of the selection plasmid pZeoSV2. The medium was changed at 24 hr. and at 48 hr the cells were split into medium containing 250 µg/ml zeocin and 1 µg/ml tetracycline. After 3-4 weeks in selection, 250 clones were picked and transferred to 96 well plates and the medium screened for HIV-1 p24 Gag antigen by immunocapture using a commercially available kit. Fifty two p24 positive clones were grown up for further analysis. The best 5 clones were determined to have p24 values of 12-23 ng/ml. Of the 5 clones, 4 were positive for VSV.G expression after tetracycline withdrawal by Western blot analysis.

The four p24/VSV.G positive clones were analyzed further for the ability to package lentiviral transfer vectors. The clones were infected with transiently produced lentiviral vector (VSV.G pseudotype) containing an expression cassette for the Green Fluorescent Protein of *A. victoria* (GFP) driven by the CMV promoter, at a multiplicity of infection of 10 and in the presence of polybrene (8 µg/ml). The infected clones then were expanded and the tetracycline removed. After 72 hours of induction, a 24 hr medium collection was performed and the supernatants were filtered and flash frozen. The frozen supernatants were titered on naive HeLa cells for transduction of the GFP gene. By FACS analysis it was determined that the population of cells (designated 10-28) created from the infection of packaging clone 10-28 had the highest titer of $5 \times 10^4$ Transducing Units (T.U.)/ml.

Figure 3:
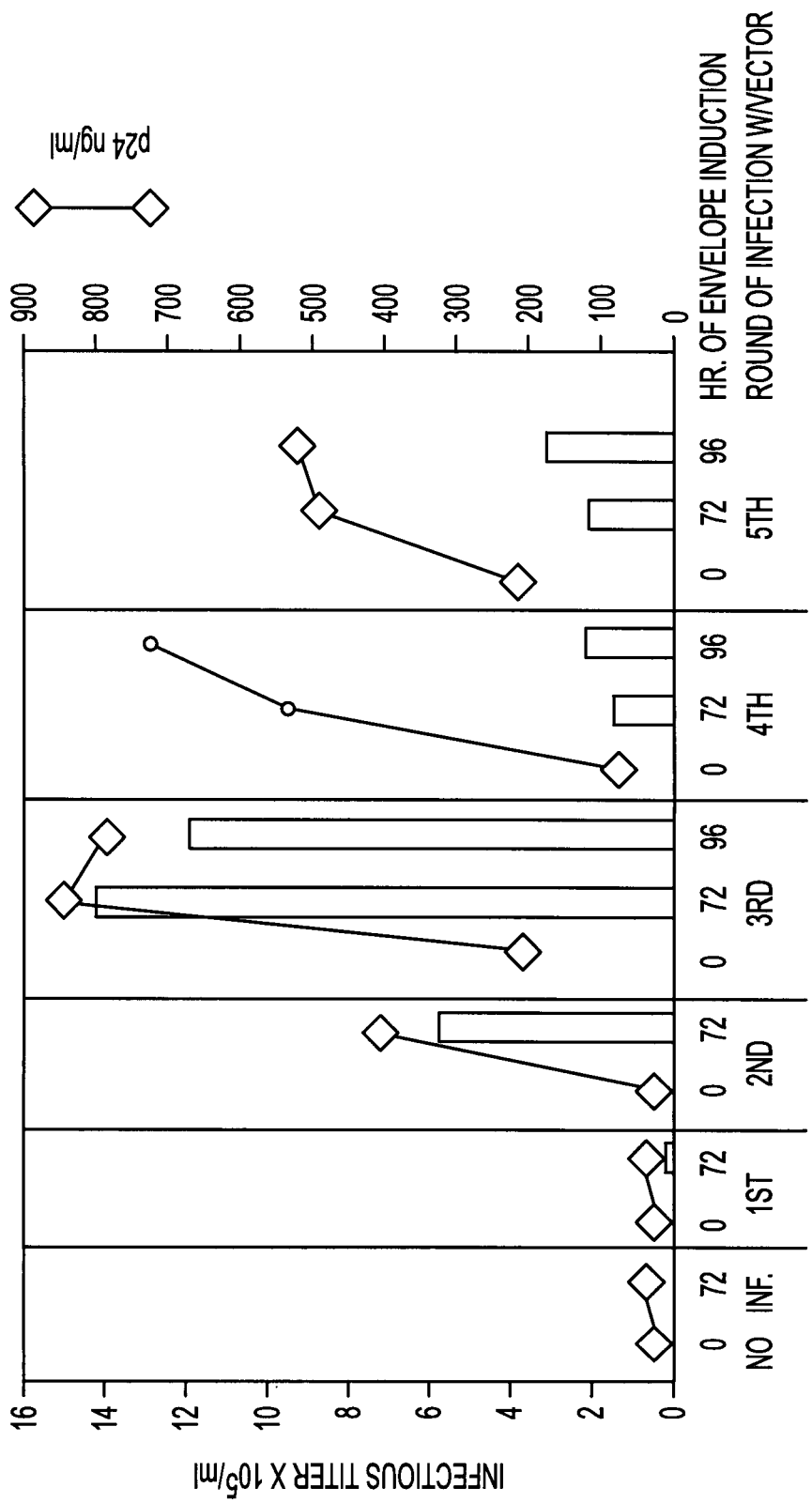
FIG. 3 is a graph depicting graded vector production with increasing amounts of transfer vector.
Figure 4:
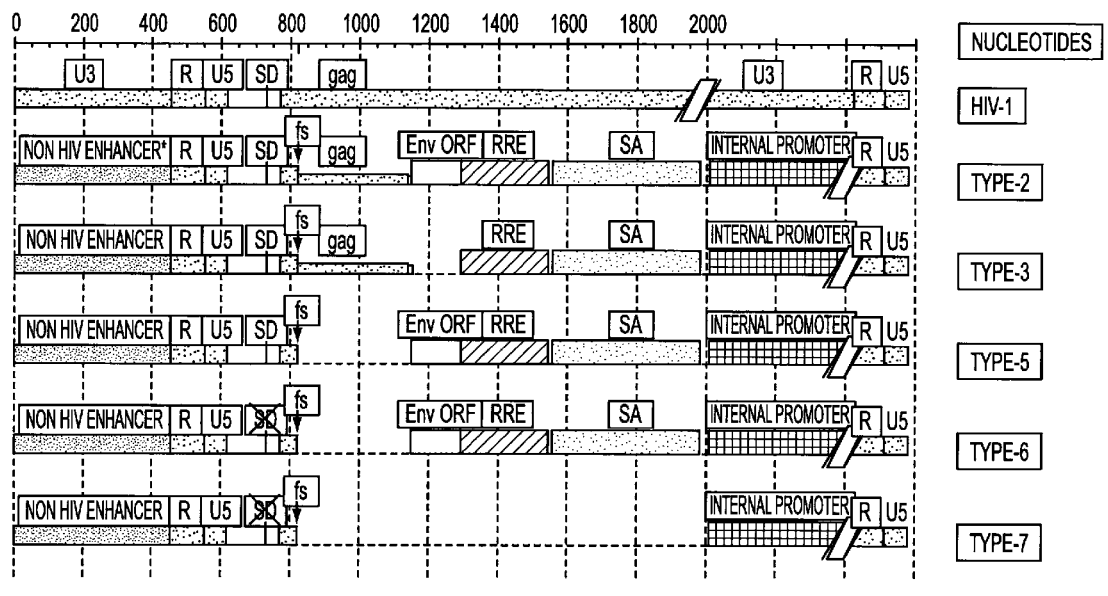
FIG. 4 depicts 5' modifications of lentivector transfer constructs. Indicated type number for a particular construct is assigned in accordance with the removal or modification of indicated elements. For instance: the construct name, such as RRL7, indicates that the vector is of the type-7 construct family and can have the RSV enhancer in the U3 region. Gag is the gag gene; fs is frameshift; Env OFR is the envelope gene reading frame; RRE is the Rev responsive element; SA is a splice acceptor; and RSV is the Rous sarcoma virus.
Figure 5:
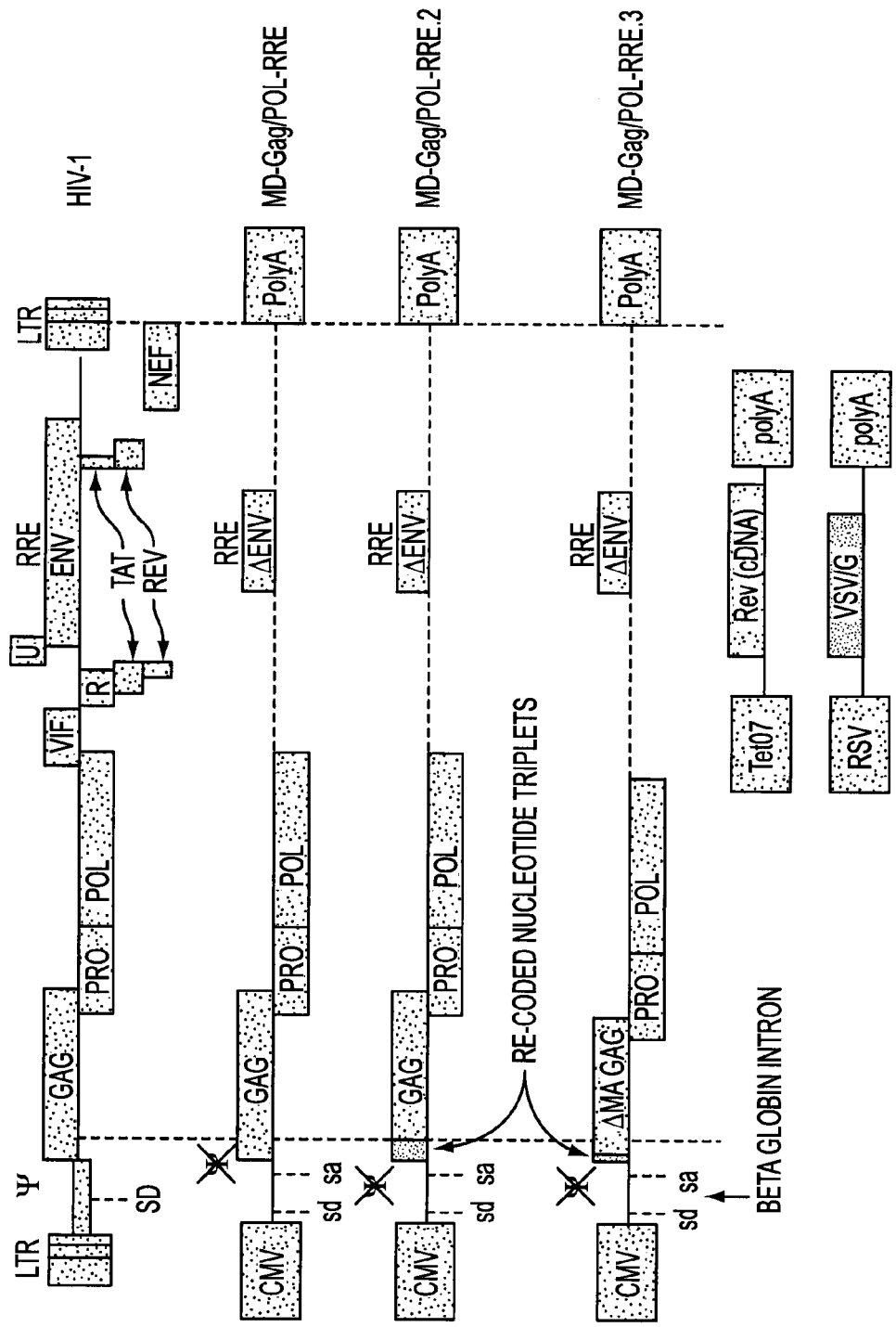
FIG. 5 depicts schematic diagrams of novel packaging constructs. Pro is protease; Δ env is a truncated envelope gene; pol is polymerase; poly A is a polyadenylation site; Tet O7 is the tet regulator, MA is matrix and VSV/G is vesicular stomatitis virus G protein.
Figure 6:
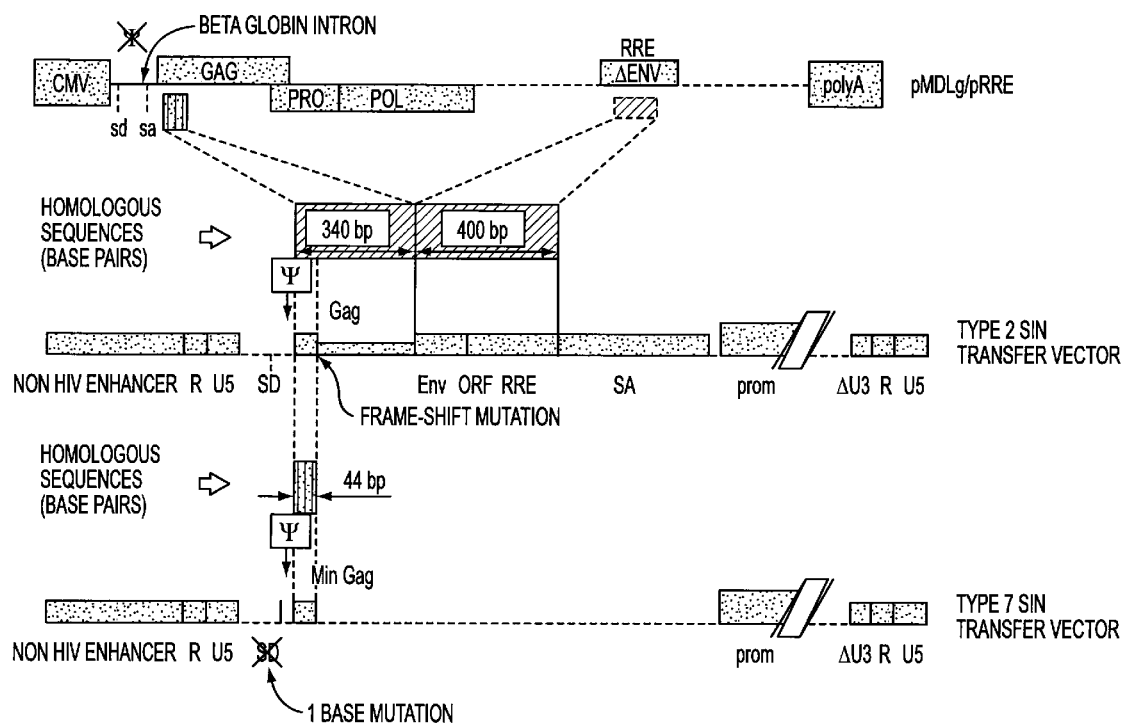
FIG. 6 depicts diagrams outlining homologous sequences between packaging (pMDLg/pRRE) and indicated transfer vector constructs. Prom is promoter and Min gag is a truncated or minimized gag.
Figure 7:
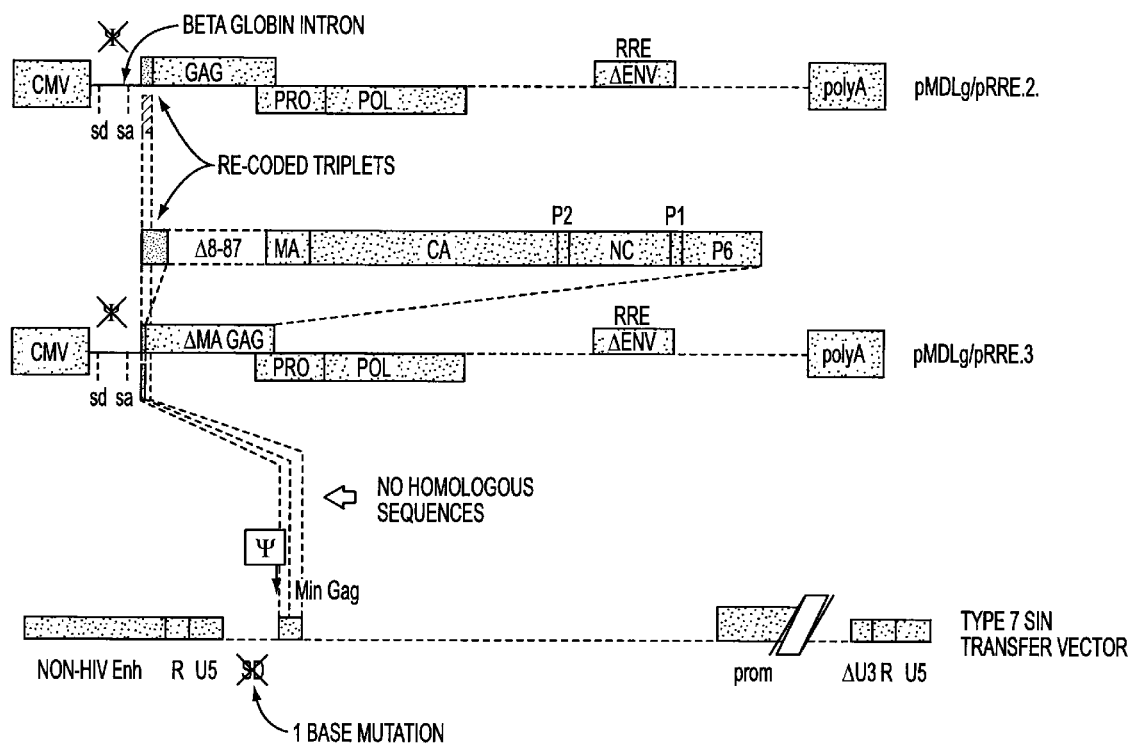
FIG. 7 depicts diagrams outlining homologous sequences between packaging constructs pMDLg/pRRE. 2 or pMDLg/pRRE. 3 and a type-7 transfer vector construct. MA is matrix; CA is capsid, P2 is gag cleavage product, NC is nucleocapsid; PI is another gag cleavage product; P6 is another gag cleavage protein and non-HIV End is a non-HIV enhancer.
Figure 8A:
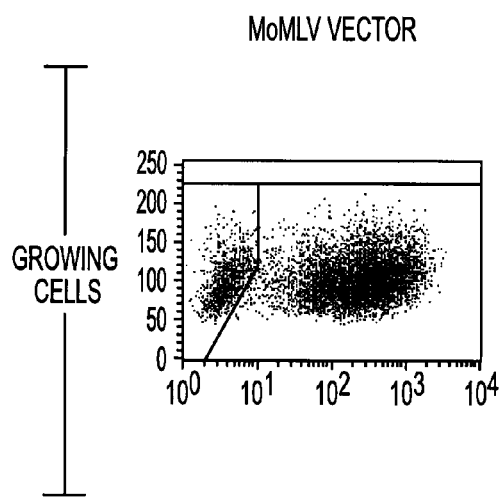
FIG. 8 depicts representations of FACS (Fluorescence Activated Cell Sorting) plots indicating high efficiency transduction of growth-arrested (by aphidicolin treatment) HeLa cells with vector particles produced by calcium phosphate transfection of nonoverlapping lentivector constructs. The following plasmids were transfected: 10 ug of CCL7sinCMVGFPpre, 5 pg of pMDLg/pRRE, or pMDLg/pRRE. 2, or pMDLg/pRRE. 3 and 3 pg of pMID.G.
Figure 8B:
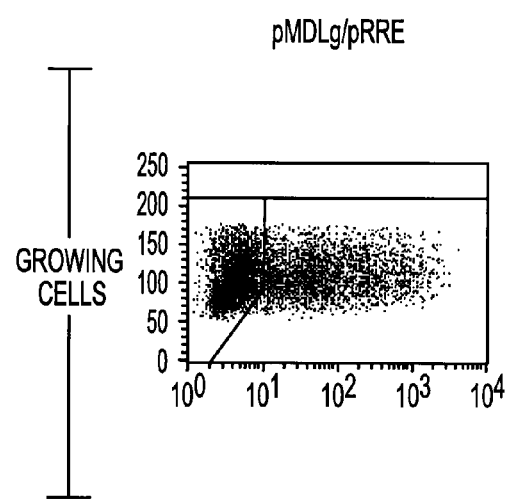
Figure 8C:
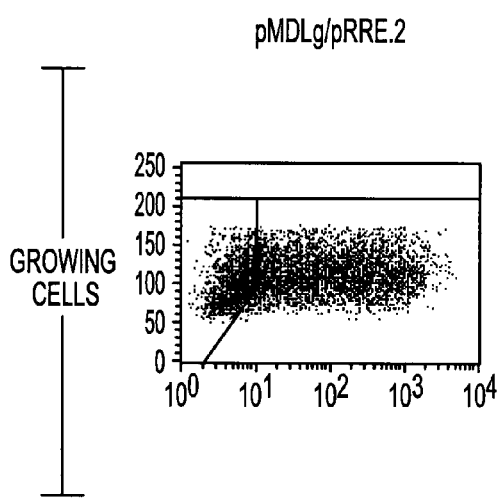
Figure 8D:
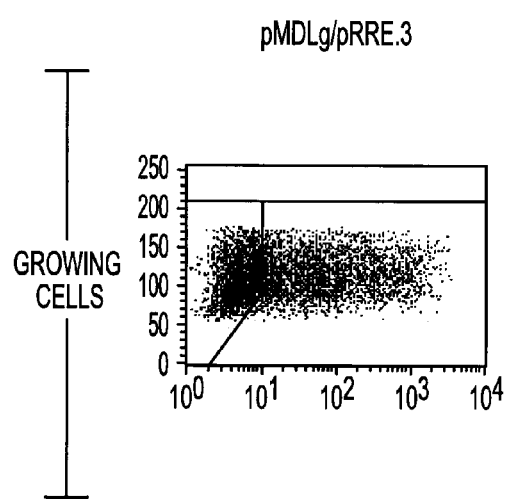
Figure 8E:
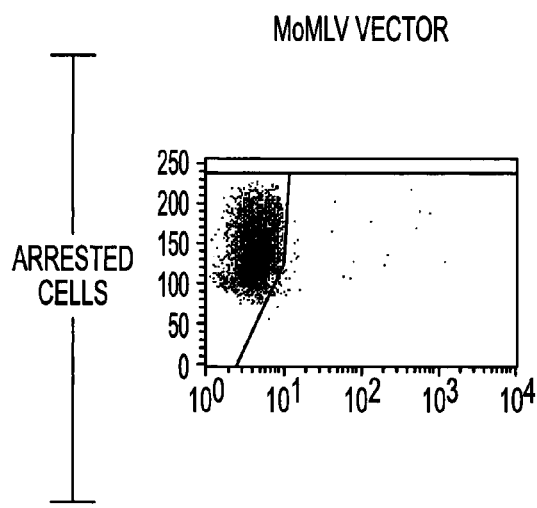
Figure 8F:
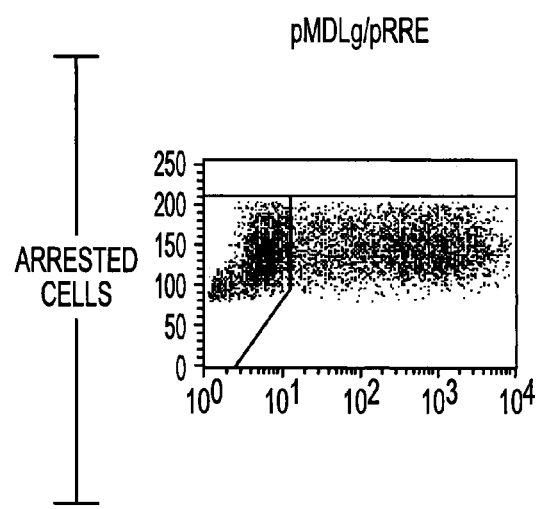
Figure 8G:
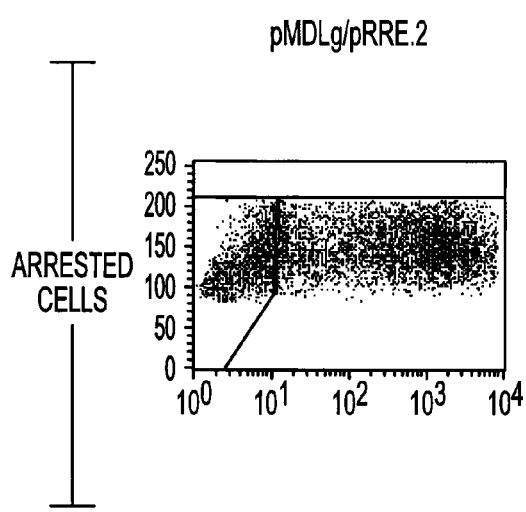
Figure 8H:
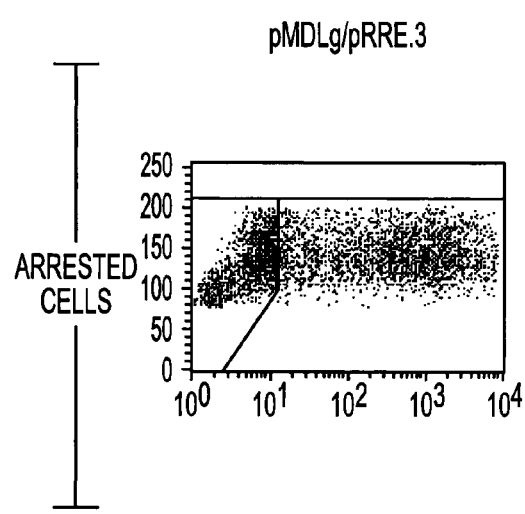
Figure 9A:
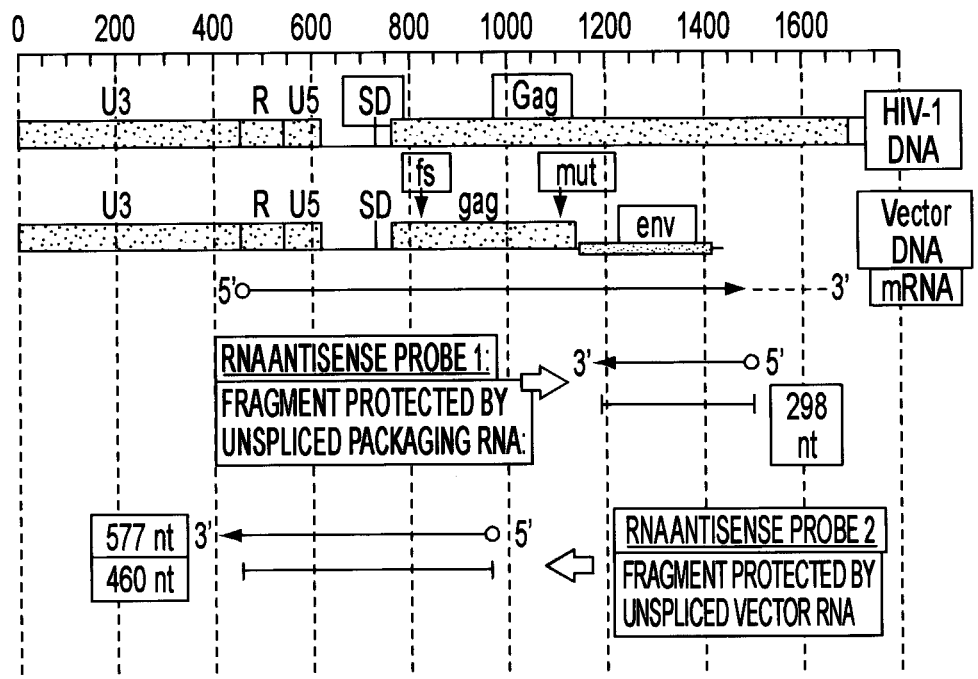
FIG. 9 depicts representations of RNA protection analyses of vector particles obtained by transient transfection of indicated plasmids. (Plasmid pCMVΔR8.2 is described in Naldini et. al. Science, supra) Mut is mutation.
Figure 9B:
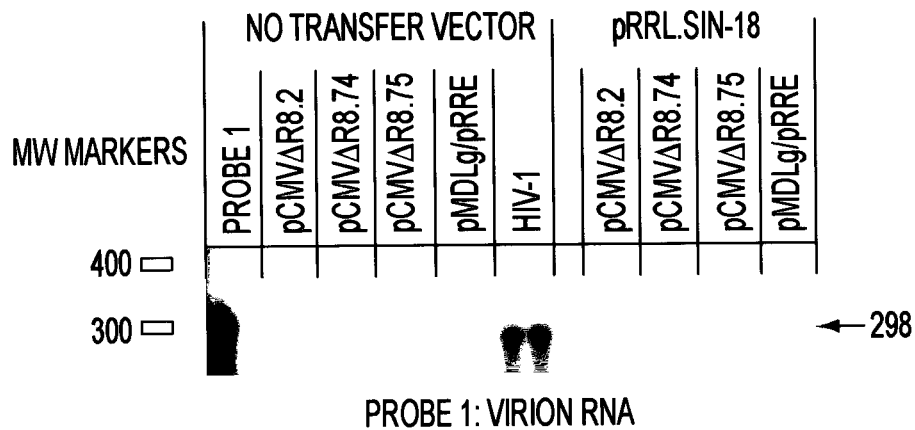
Figure 9C:
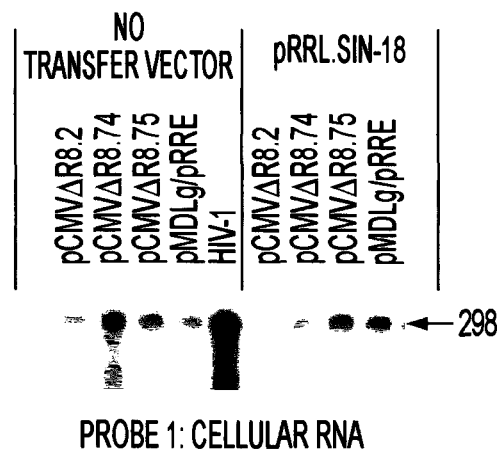
Figure 9D:
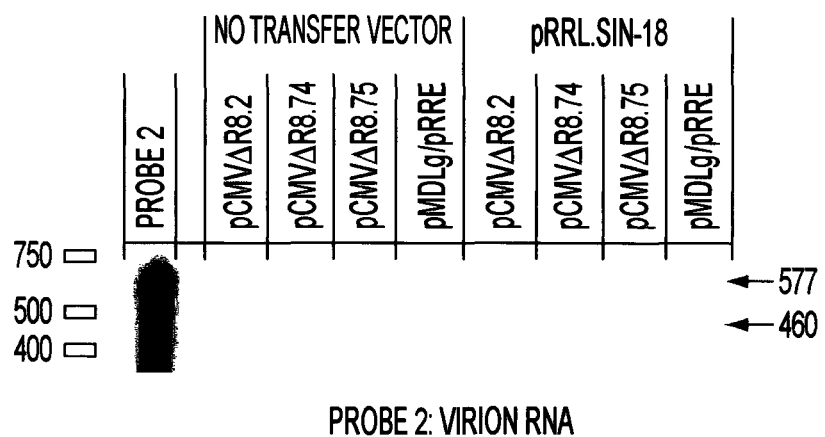

The infected packaging population, 10-28, was used for the creation of high titer producer clones of GFP lentiviral vector. 10-28 cells were sorted by FACS and the highest GFP expressing cells were retained and expanded. That population then was infected serially ("pinged") an additional 4 times with transiently produced GFP lentiviral (VSV.G pseudotype). After each infection the supernatants were collected after a 72-96 hr of VSV.G induction. Supernatants were titered on HeLa cells and analyzed for p24 content by immunocapture assay. Infectious titers peaked after the third ping reaching $1.5 \times 10^6$ T.U./ml (see FIG. 3). The population of cells from the third ping then were subcloned to isolate high titer vector producers.

EXAMPLE 6

Lentiviral Packaging Constructs pMDLg/p is a CMV driven expression plasmid that contains only the gag/pol coding sequences from HIV-1. First, pkat2Lg/p was constructed by ligating a 4.2 kb ClaI-EcoRI fragment from pCMVΔR8.74 with a 3.3 kb EcoRI-HindIII fragment from pkat2 (Finer et al., Blood (1994) 83: 43-50) and a 0.9 kb HindIII-NcoI fragment from pkat2 along with a NcoI-ClaI DNA linker consisting of synthetic oligonucleotides 5'-CATGGGTGCGAGAGCGTCAGTAT-TAAGCGGGGGAGAATT AGAT-3' (SEQ ID NO: 21) and 5'-CGATCTAATTCTCCCCCGCTTAATACT-GACGCTCTCG CACC-3' (SEQ ID NO: 22). Next, pMDLg/p was constructed by inserting the 4.25 kb EcoRI fragment from pkat2Lg/p into the Eco RI site of pMD-2. pMD-2 is a derivative of pMD.G (Ory et al., supra) in which the pXF3 plasmid backbone of pmD.G has been replaced with a minimal pUC18 (Invitrogen) plasmid backbone and the 1.6 kb VSV.G encoding EcoRI fragment has been removed.

pMDLg/pRRE differs from pMDLg/p by the addition of a 374 bp RRE-containing sequence from HIV-1 (HXB2) immediately downstream of the pol coding sequences. To generate pMDLg/pRRE, the 374 bp NotI-HindIII RRE-containing fragment from pHR3 was ligated into the 9.3 kb NotI-BglII fragment of pVL 1393 (Invitrogen) along with a Hindm-Bgin DNA linker consisting of synthetic oligonucleotides 5'-AGCTTCCGCGGA-3' (SEQ ID NO: 23) and 5'-GATCTCCGCGGA-3' (SEQ ID NO: 24) to generate pVL1393RRE (pHR3 was derived from pHR2 by the removal of HIV env coding sequences upstream of the RRE sequences in pHR2), A Not I site remains at the junction between the gag and RRE sequences. pMDLg/pRRE then was constructed by ligating the 380 bp Eco RI-SstII fragment from pV1393RRE with the 3.15 kb SstII-NdeI fragment from pMD-2FIX (pMD-2FIX is a human factor IX containing a variant of pMD-2 which has an SstII site at the 3' end of the Factor IX insert), the 2.25 kb NdeI-AvrII fragment from pMDLg/p and the 3.09 kb AvrII-EcoRI fragment from pkat2Lg/p (Finer et al., supra).

pMDLg/pRRE, 2 is a gag/pol expressing lentiviral packaging vector in which the codons for the gag amino acids 2-13 have been mutated (without changing the amino acids sequence). pMDLg/pRRE. 2 was generated by ligating an 8.4 kb ClaI-Bsu36I fragment and a 1.4 kb Bsu36I-EcoRI fragment from pMDLg/pRRE with a DNA linker consisting of synthetic oligonucleotide, 5'-aattgagatctccgccatgggagc-ccggggccagcgtcctgtctggagggagggac-3' (SEQ ID NO, 25) and 5'-cggtccagctcccctcagacaggagggc-ccgggctcccatggcgggcagatctcg-3' (SEQ ID NO, 26).

pMDLg/pRRE. 3 is a gag/pol expressing lentiviral packaging vector in which the codons for the gag amino acids 2-7 have been mutated (without changing the amino acids sequence) and in which gag coding sequences for amino acids from 8 to 87 of Gag polyprotein have been deleted. Previously described experiments which were conducted to study HIV-1 MA protein functions (Reil et al., EMBO J. (1998) 17: 2699-708) demonstrated that deletion of amino acids from 8 to 87 of matrix protein (MA), which is part of Gag polyprotein, has no effect on efficiency of wild type HIV-1 entry into infected cell, when analyzed virions were pseudotyped with VSV/G. pMDLg/pRRE.3 was generated by ligating an 6.8 kb SphI-Bsu36I fragment and a 1.4 kb Bsu361-EcoRI fragment from pMDLg/pRRE with a 0.4 kb XbaI-SphI fragment from plasmid HXB 10ACT. A8-87 described in (Reil et al., supra) and a DNA linker consisting of synthetic oligonucleotides 5' aat-tcgagatctgccgccgccatgggagcccgggccagcgtc-3' (SEQ ID NO: 27) and 5'-ctagagacgctggccc gggctcccatggcggcggcagatctcg-3' (SEQ D NO: 28).

ptetMDrev is an expression vector in which HIV-1 Rev protein expression is under the control of the tet inducible tet° 7CMV hybrid promoter. The only HIV sequences contained in the vector are HXB2 rev cDNA comprising the first (nucleotides 5937 through 6045) and second (nucleotides 8379 trough 8653) exons (Genbank accession number K03455). To generate ptetMDrev, the CMV enhancer/promoter of pMD-2 was replaced with the tet°/CMV hybrid promoter from ptet/splice (Gibco/BRL), yielding ptetMD. Next, ptetMDNcol (ATG) was generated by inserting a DNA linker consisting of synthetic oligonucleotides 5'-aattcacgcgtgcc gcaccatgcag-gaagaagcggagacagcgacgaagaccttcgcgccgccagtagctgt-3' (SEQ ID NO: 29) and 5'-aaffacagctactggeggccgcgaggag-gtcttgtcgctgttccgctcttcctgccatgtggcggaggg-3' (SEQ ID NO.: 30) into EcoRI-digested ptetMD. Finally, ptetMDrev was generated by ligating a 4.6 kb AlwNI-BamHI fragment and a 615 bp Bam HI-BbsI fragment from ptetMDNcol (ATG) with a 354 bp BbsI-AlWNI fragment from pRSVrev (plasmid described in Dull et al., J Virol. (1998) 72: 8463-71).

EXAMPLE 7

Construction of Lentiviral Transfer Vectors pHR7 is a maximally deteted lentiviral vector in which all HIV sequences between nt 43 of the gag coding sequence and the transgene have been deleted to further decrease homology between the transfer and packaging vectors. pHR7 was derived from pHR6 by ligating a 8.2 kb SacII-Not I fragment and a 1.3 kb XhoI-SacII fragment from pHR6 with a DNA linker consisting of synthetic oligonucleotides 5'-GGCCAT-TGAC-3' (SEQ ID NO: 31) and 5'-TCGAGTCAAT-3' (SEQ ID NO: 32).

pCCL7sinCMVGFPpre is a lentiviral vector which incorporates the maximally deleted 5' untranslated region of pHR7 with a self inactivating 3' LTR, a CMV 5' U3 and a post transcriptional regulatory (pre) element from the woodchuck hepatitis virus. To generate pCCL7sinCMVGFPpre, first a 329 bp AflII-XhoI fragment from pHR7 was ligated to a 1.9 kb XhoI-AvrII fragment and a 3.2 kb AvrII-AflII from pRRLsnI8hPGK.GFP to generate pRRL7sinhPGK.GFP. Next, the hPGK internal promoter was replaced by a hCMV internal promoter by ligating a 606 bp ClaI-BamHI fragment (in which the ClaI site was "filled") from pRRLsinCMV.GFP with a 4.9 kb BamHI-AvaI fragment (in which the AvaI site was "filled") from pRRL7sinhPGK.GFP to generate pRRL7sinhCMV.GFP. Next a 600 bp SalI to EcoRI woodchuck hepatitis virus pre fragment (generated by PCR using pWHV8 (Genbank accession number J04514) as the template with primers 5'-tctagaggatccgtcgacaatcaacctctggattacaa-3' (SEQ ID NO: 33) and 5'-gagctcgaattccaggcggggaggcggc-ccaa-3' (SEQ ID NO, 34) followed by digestion with SalI and EcoRI) was inserted into SalI and EcoRI digested pRRL7sinhCMV.GFP to generate pRRL7sinhCMV.GFPpre. Next the 704 bp AflII to AflII fragment of RRL7sinhCMV.GFP was replaced with the 1147 bp AflII to AflII fragment from pCCL to generate pCCL7sinhCMV.GFPpre.

EXAMPLE 8

Construction of conditional self-inactivating vectors (cSIN)

pRRLsin36PGKGFPtet° 3' is a lentiviral vector in which the 3' LTR contains a hybrid tet°/HIV U3. The hybrid 3' U3 consists of seven copies of the tet operator (tet°7) linked to the 36 nucleotides of the 3' portion of the HIV U3, which includes the "TATA" box. pRRLsin36PGKGFPtet°3' is a conditional self-inactivating (cSIN) vector that, after transduction, can be activated to express full-length packagable vector transcripts only in the presence of tetracycline responsive transactivator (tTA)—for example, after transduction of an appropriate packaging cell line expressing tTA. After transduction of any cells not expressing tTA, the resulting 5'tet°/HIV U3 is transcriptionally non-functional, even in the presence of HIV Tat protein, which is known to upregulate basal transcriptional activity of heterologous promoters. That significantly reduces the chance of mobilization of the vector genome even if transduced cells are infected by the wild type HIV-1.

pRRLsin36PGKGFPtet°3' allows for a novel approach for a SIN vector design and vector system in general. The approach is based on the fact, that such a vector can be used for serial transductions ("pings") into tTA-expressing packaging cell lines to obtain a high-titer producer clone while maintaining the SIN phenotype in non-tTA expressing target cells.

To generate pRRLsin36PGKGFPtet°3', first a 5.6 kb Asp718-BamHI fragment from pRRL5sinI 8PGKGFP was ligated to a 303 bp XhoI-Asp718 fragment from ptet/splice (Gibco/BRL) along with the DNA linker consisting of synthetic oligonucleotides 5'-GATCCCGGGC-3' (SEQ ID NO: 35) and 5'-TCGAGCCCGG-3' (SEQ ID NO: 36) to generate ptetINT (pRRL5sinI8PGKGFP is a vector in which the untranslated region of pRRLsnI8PGKGFP (Zufferey et. al., J. Virol., (1998) 72: 9873-9880) has been replaced with the corresponding region from pHR5) Next a 2.8 kp AflIII-Asp718 fragment from ptetINT was ligated to a 3.1 kb BclI-AflE fragment from pRRLsin36PGKGFP (Zufferey et. al. (1998) supra) along with the DNA linker consisting of synthetic oligonucleotides 5'-GTACCCGGGTCGAGTAG-GCTT-3' (SEQ ID NO: 37) and 5'-GATCAAGCCTACTC-GACCCGG-3' (SEQ ID NO: 38) to generate ptet36INT. Finally a 3.4 kb BamHI-AflIII fragment from ptet36INT was ligated to a 3.6 kb AflII-BclI fragment from pRRLsin36PGKGFP to yield pRRLsin36PGKGFPtet°3'.

pCCL7sinCMVGFPpreTet 3' is a lentiviral transfer vector maximally deleted in the 5' untranslated region, in which the 3' LTR of pCCL7sinCMVGFPpre has been replaced with the tet-responsive 3' LTR from pRRLsin36PGKGFPtet°3'. pCCL7sinCMVGFPpreTet°3' was generated by ligating a 3.44 kb AflIII-EcoRI fragment from pCCL7sinCMVGFPpre with a 3.5 kb EcoRI-AflIII fragment from pRRLsin36PGKGFPtet°3'.

EXAMPLE 9

To isolate viral RNA, 0.45 micron-pore-size (Millipore) filtered supernatants containing vector particles were adjusted for p24 content and microcentrifuged at 14,000 rpm to pellet the virions. Supernatants were aspirated and 50 µg of yeast RNA were added to each pellet as carrier. Total RNA was isolated from the samples using RNAqueous kit (Ambion) according to manufacturer instructions. DNA probe template for in vitro transcription was prepared by two cycles of PCR using a Lig'nScribe kit (Ambion) as instructed by the manufacturer. Probe 1 was generated by PCR using primers 5'-CATCAGGCCATATCA CCTAGA-3' (SEQ ID NO: 39) and 5'-GTACTAGTAGTTCCTGCTATGT-3' (SEQ ID NO: 40) and plasmid pCMVΔR8.74 to amplify a 298 bp fragment containing nucleotides 1215 through 1513 of HIV-1 HXB2 (Genbank accession number K03455). Probe 2 was generated by PCR using primers 5'-CTGCTGACATCGAGCT TGC-TACA-3' (SEQ ID NO: 41) and 5'-CTAGCTCCCTGCT TGCCCATACT-3' (SEQ ID NO: 42) and plasmid pHR2 as template to amplify a 577 bp fragment containing nucleotides 336 through 913 of HIV-1 HXB2 (Genbank accession number K03455). $^{32}$P antisense riboprobe then was synthesized by T7 RNA polymerase in the presence of [α-$^{32}$P]UTP (800 Ci/ml, DuPont NEN). Full length probes were gel purified and stored in 0.5 M ammonium acetate, 1 mM EDTA, and 0.2% SDS elution buffer at −20° C. RNA protection assay was performed using a HybSpeed™ kit (Ambion) according to manufacturer instructions. RNAse A/T1 mix (0.5 U/20 U per reaction, Ambion) digestion protected probe fragments were separated on 4% polyacrylamide, TBE and 8 M urea gels. For fragment size determination, $^{32}$P-labeled an RNA markers were synthesized on RNA Century™ template set and electrophoresed in parallel. For band detection and intensity quantification, dried gels were exposed either to photofilm or a phosphorimager plate (Molecular Dynamics).

EXAMPLE 10

Transfer Vector Constructs. pHR'CMV-LacZ and pHR'CMV-Luciferase have been described (Naldini et al., Science, supra). pHR2 is a lentiviral transfer vector in which the polylinker and downstream nef sequences up to the KpnI site of pHR' have been replaced with a ClaI/SpeI/SnaBI/Sma VBamHI/SacII/EcoRI polylinker. pHR2 was generated by replacing the 3.7 kb ClaI-SacI fragment of pHR'CMVlacZ with a 607 bp ClaI-SacI fragment generated by PCR using pHR'CMVlacZ as the template with oligonucleotide primers 5'-CCATCGATGGACTAGTC CTACGTATCCCCGGG-GACGGGATCCGCGGAATTCCGTTTAA-GACCAATGAC-3' (SEQ ID NO: 43) and 5'-TTATAATGT-CAAGGCCTCTC-3' (SEQ ID NO, 44), followed by digestion with ClaI and Sacs.

pHR2PGK-NGFR, pHR2CMV-NGFR and pHR2MFG-NGFR are lentiviral transfer vectors in which the truncated low affinity NGF receptor (Bordignon et al. Hum. Gene Therap. (1995) δ: 813-819) transgenes under the control of the murine PGK, human CMV or Moloney Leukemia Virus promoter, respectively, have been inserted into the polylinker of pHR2. The pHR2PGK-NGFR transgene encodes no intron sequences while the pHR2CMV-NGFR vector includes the intron from plasmid pMD (Ory et al., supra) and the pHR2MFG-NGFR vector contains the MLV intron from MFG-S (Ory et al., supra).

pRRL, pRLL, pCCL and pCLL are lentiviral transfer vectors containing chimeric Rous Sarcoma Virus (RSV)/HIV or CMV/HIV 5' LTR's and vector backbones in which the SV40 polyadenylation and (enhancerless) origin of replication sequences have been included downstream of the HIV 3' LTR replacing most of the human sequence remaining from the HIV integration site. In pRRL, the enhancer and promoter (nucleotides −233 to −1 relative to the transcriptional start site: Genbank accession number J02342) from the U3 region of RSV are joined to the R region of HIV-1 LTR. In pRLL the RSV enhancer (nucleotides −233 to −50) sequences are joined to the promoter region (from position −78 bp relative to the transcriptional start site) of HIV-1. In pCCL, the enhancer and promoter (nucleotides −673 to −1 relative to the transcriptional start site, Genbank accession number K03104) of CMV was joined to the R region of HIV-1. In pCLL, the CMV enhancer (nucleotides −673 to −220) was joined to the promoter region (position −78 bp) of HIV-1.

pHR2hPGK-GFP, pCCLhPGK-GFP, pCLLhPGK-GFP, pRRLhPGK-GFP, pPLLhPGK.GFP are lentiviral transfer vectors containing the enhanced Green Fluorescent Protein (750 bp BamHI-NotI fragment from pEGFP-I (Clontech)) coding region under the control of the human PGK promoter (nucleotides 5-516, Genbank accession number M11958), inserted into the polylinker region of each parental vector. pRRLGFP was obtained by deletion of the XhoI-BamHI fragment containing the PGK promoter from pPRLhPGK-GFP.

pRRLhPGK.GFP.SIN-18 is a vector in which 3' LTR sequences from −418 to −18 relative to the U3/R border have been deleted from pRLhPGK.GFP.

Packaging Constructs. The tat-defective packaging construct pCMVΔR8.93 was obtained by swapping a EcoRI-SacI fragment from the plasmid R7/pneo (−) (Feinberg et al., PNAS (1991) 88: 4045-4049) with the corresponding fragment of pCMVΔR8.91, a previously described Gag, Pol, Tat, and Rev expressing plasmid (Zufferey et al., 1997, supra). The fragment has a deletion affecting the initiation codon of the tat gene and a frameshift created by the insertion of a MluI linker into the Bsu361 site as described previously. pCM-VΔR8.74 is a derivative of pCMVΔR8.91 in which a 133 bp SacI fragment, containing a splice donor site, has been deleted from the CMV-derived region upstream of the HIV sequences to optimize expression.

pMDLg/p is a CMV driven expression plasmid that contains only the gag/pol coding sequences from HIV-1. First, pkat2Lg/p was constructed by ligating a 4.2 kb ClaI-Eco RI fragment from pCMVΔR8.74 with a 3.3 kb EcoRI-HindIII fragment from pkat2 (Finer et al. supra) and a 0.9 kb HindIII-NcoI fragment from pkat2 along with a NcoI-ClaI linker consisting of synthetic oligonucleotides, 5'-CATGGGTGC-GAGAGCGTCAGTATTAAGCGGGGGAGAATTAGAT-3' (SEQ ID NO: 45) and 5'-CGATCTAATTCTCCCCCGCT-TATACTGACGCTCTCGCACC-3' (SEQ ID NO: 46). Next, pMDLg/p was constructed by inserting the 4.25 kb EcoRI fragment from pkat2Lg/p into the Eco RI site of pMD-2. pMD-2 is a derivative of pMD.G (Ory et al., supra) in which the pXF3 plasmid backbone of pMD.G has been replaced with a minimal pUC plasmid backbone and the 1.6 kb VSV.G encoding EcoRI fragment has been removed.

pMDLg/pRRE differs from pMDLg/p by the addition of a 374 bp RRE-containing sequence from HIV-1 (HXB2) immediately downstream of the pol coding sequences. To generate pMDLg/pRRE, the 374 bp NotI-HindIII RRE-containing fragment from pHR3 was ligated into the 9.3 kb NotI-BglII fragment of pVL1393 (Invitrogen) along with a HindIII-BglII oligonucleotide linker consisting of synthetic oligonucleotides 5'-AGCTTCCGCGGA-3' (SEQ ID NO: 47) and 5'-GATCTCCG CGGA-3 (SEQ ID NO: 48) to generate pVL1393RRE (pHR3 was derived from pHR2 by the removal of HIV env coding sequences upstream of the RRE sequences in pHR2). A Not I site remains at the junction between the gag and RRE sequences. pMDLg/pRRE was then constructed by ligating the 380 bp Eco RI-SstII fragment from pV1393RRE with the 3.15 kb SstII-NdeI fragment from pMD-2FIX (pMD-2FIX is a human factor IX containing variant of pMD-2 which has an SstII site at the 3' end of the Factor IX insert), the 2.25 kb NdeI-AvrII fragment from pMDLg/p and the 3.09 kb AvrII-EcoRI fragment from pkatILg/p (Finer et al., supra).

pRSV-Rev and pTK-Rev (generous gifts of T. Hope, Salk Institute) are rev cDNA expressing plasmids in which the joined second and third exons of HIV-1 rev are under the transcriptional control of either the RSV U3 or the Herpes Simplex Virus 1 thymidine kinase promoter, respectively. Both expression plasmids utilize polyadenylation signal sequences from the HIV LTR in a pUC118 plasmid backbone.

Vector production and assays. Vectors were produced by transient transfection into 293T cells as previously described (Naldini et al., PNAS, supra) with the following modifications. About $5 \times 10^6$ 293T cells were seeded in 10 cm dishes 24 hr prior to transfection in IMDM culture media (JRH Biosciences) with 10% FBS and penicillin (100 IU/ml) and streptomycin (100 µg/ml) in a 5% $CO_2$ incubator and the culture medium was changed 2 hr prior to transfection. A total of 20 µg of plasmid DNA was used for the transfection of one dish, 3.5 µg of the envelope plasmid pMD.G, 6.5 µg of packaging plasmid and 10 µg of transfer vector plasmid. The precipitate was formed by adding the plasmids to a final volume of 450 µl of 0.1×TE (TE: 10 mM Tris pH=8.0, 1 mM EDTA) and 50 µl of 2.5M $CaCl_2$, mixing well, then adding dropwise 500 µl of 2×HBS (281 mM NaCl, 100 mM HEPES, 1.5 mM $Na_2HPO_4$., pH=7.12) while vortexing, and immediately adding the precipitate to the cultures. The medium (10 ml) was replaced after 14-16 hrs and the conditioned medium was collected after another 24 hr. cleared by low-speed centrifugation and filtered through 0.22 pm cellulose acetate filters. For in vitro experiments serial dilutions of freshly harvested conditioned medium were used to infect $10^5$ cells in a 6-well plate in the presence of 8 µg/ml polybrene. Viral p24 antigen concentration was determined by immunocapture (Alliance, DuPont-NEN). Vector batches were tested for the absence of replication-competent virus by monitoring p24 antigen expression in the culture medium of transduced SupTI lymphocytes for three weeks. In all cases tested, p24 was undetectable (detection limit 3 pg/ml) once the input antigen had been eliminated from the culture. Northern Blot Analysis. Total RNA was isolated from $1-2 \times 10^7$ cells harvested at confluency using RNAsol B as suggested by the manufacturer. About 10-20 µg of RNA were loaded per well on 1% agarose gets using NorthernMax (Ambion, Austin Tex.) reagents as described by the manufacturer. Transfer was to Zetabind membrane (Cuno Inc., Meridien Conn.) either by capillary transfer or by pressure blotting (Stratagene). $^{32}P$ labeled probes were made by random priming.

Intracerebral injection of Vectors. Twelve Fischer 344 mare rats weighing approximately 220 g were obtained from Harlan Sprague-Dawley (Indianapolis, Ind.), housed with access to ad libitum food and water on a 12 hr light/dark cycle and were maintained and treated in accordance with published NIH guidelines. All surgical procedures were performed with the rats under Isofluorane gas anesthesia using aseptic procedures. After a rat was anesthetized in a "sleep box" it was placed in a small animal stereotaxic device (Kopf Instruments, Tujunga, Calif.) using the earbars which do not break the tympanic membrane. The rats were randomly divided into one control and four treatment groups. After the rats were placed in the stereotaxic frame, 2 µl of lentiviral vector concentrated by ultracentrifugation at 50,000×g for 140 min at 20° C. (Naldini et al., PNAS, supra) in phosphate buffered saline (PBS) were injected consecutively into the striatum in both hemispheres over 4 minutes at a rate of 0.5 µl per minute (AP 0.0, LAT±3.0, DV −5.5, −4.5, −3.5 with the incisor bar set at −3.3 mm below the intraaural line; Paxinos & Watson. "The Rat Brain In Stereotaxic Coordinates" (1987) Academic Press, SD) using a continuous infusion system. During the injection, the needle was slowly raised 1 mm in the dorsal direction every 40 seconds (3 mm total withdrawal). One minute after the cessation of the injection the needle was retracted an additional 1 mm and then left in place for an additional 4 minutes before being slowly withdrawn from the brain.

Histology. One month after vector injection each animal was deeply anesthetized with i.p. pentobarbital and perfused through the aorta with sterile PBS, followed by ice cold 4% paraformaldehyde (PFA) perfusion. The brains were removed from the skull, postfixed in 4% PFA by immersion for 24 hr and then transferred into a 30% sucrose/PBS solution for 3-4 days until the brains sank to the bottom of the containers. The brains then were frozen on dry ice and 40 µm thick coronal sections were cut on a sliding microtome, Sections were collected in series in microtitre-well plates that contained a glycerin based anti-freeze solution and they were kept at −30° C. until further processing. Immunocytochemistry was performed following the general procedure described previously (Sternberger et al. J. Histochem. Cytochem. (1970) 18: 315-333). After several PBS rinses and an incubation in 3% hydrogen peroxide, the sections were placed in a 3% normal goat serum (NGS). The sections then were incubated in the primary anti-GFP antibody (1:1000, Clontech, Palo Alto, Calif.) in 1% NGS and 0.1% Triton X-100 overnight at room temperature. After rinsing the sections were incubated in the biotinylated rabbit-anti-goat secondary antibody (Vector, Burlingame, Calif.) for 3 hours. After rinsing, the sections were incubated with horseradish peroxidase streptavidin and then reacted using the purple chromagen kit VIP (Vector), mounted dried dehydrated, and coverslipped.

Tat is required to produce vector of efficient transducing activity. To investigate the role of Tat in the production of transducing particles, expression from lentiviral vectors was first examined by Northern analysis. The patterns of RNA's induced by transfer vectors in which the transgene was driven by an internal PGK, CMV, or retroviral MFG promoter were studied in both producer and target cells. In transfected 293T cells, expression occurred mainly from the internal promoter. When a packaging construct expressing both Tat and Rev was cotransfected a dramatic enhancement of transcription from the LTR was observed, with an accumulation of unspliced vector RNA. In cells transduced with the vectors, that is, in the absence of Tat and Rev, transcription from the LTR was suppressed almost completely, the residual transcripts underwent splicing and the internal promoter was responsible for most of the expression.

A packaging plasmid carrying two mutations in tat (pCMVΔR8.93) then was constructed. The first mutation is a deletion of the T in the ATG initiation codon of the tat genes the second an insertion of a Mlu I linker producing a translation stop codon after residue 46 of the Tat protein. These changes confer a tat-defective phenotype to HIV-1 (Feinberg et al., supra). After transfection of the control or tat-defective packaging constructs into 293T cells, comparable yields of vector particles were recovered in the culture medium, as assayed by the Gag p24 antigen (see Table 2). Such Tat-independence was expected from the replacement of the HIV LTR by the constitutive CMV promoter in the packaging construct. However, the particles produced in the absence of Tat had a dramatically reduced transducing activity (Table 3): 5 to 15% of that of particles produced by the control Tat-positive packaging construct.

TABLE 2

GFP transduction into HeLa cells by lentiviral vectors made by transfer constructs with wild-type or 5'chimeric LTR and packaging constructs with or without a functional tat

| Transfer Construct | tat Gene in Packaging Construct | End-point Titer (T.U./ml) | p24 Antigen (ng/ml) | Transduction Efficiency (T.U./ng p24) |
|---|---|---|---|---|
| pHR2 | + | $4.1 \times 10^6$ | 297 | 13,805 |
| pHR2 | − | $2.4 \times 10^5$ | 545 | 440 |
| PRRL | + | $1.3 \times 10^7$ | 546 | 23,810 |
| PRRL | − | $4.9 \times 10^6$ | 344 | 14,244 |

Vectors carrying a PGK-eGFP expression cassette were produced by the transfection of the indicated transfer and packaging plasmid plus the pMD.G plasmid into 293T cells. Serial dilutions of transfectant conditioned medium were incubated with HeLa cells, and the cultures were scored after 6 days. For calculating end-point titer samples were selected from the linear portion of the vector dose response curve. The average of duplicate determination is shown for a representative experiment of five performed T.U. is transducing units.

TABLE 3

Transducing activity of lentiviral vectors made with and without a functional tat gene in the packaging construct.

| Transfer Vector | Target Cells | Transducing Activity (Transduction Unit/ng p24) | |
|---|---|---|---|
| | | With Tat In Packaging Construct | Without Tat In Packaging Construct |
| pHR'CMV-LacZ | 293T | $1,056 \pm 54^a$ | $152 \pm 26^a$ |
| pHR2PGK-eGFP | HeLa | $5,666^b$ | $384^b$ |
| pHR'CMV-Luciferase | HeLa | $3,000 \pm 152^c$ | $152 \pm 26^c$ |
| pHR'CMV-Luciferase | HeLa-tat | $3,777 \pm 348^c$ | $486 \pm 59^c$ |
| pHR'Luciferase[d] | HeLa | $46 \pm 1^c$ | $0.3 \pm 0.003^c$ |
| pHR'Luciferas[d] | HeLa-tat | $3,296 \pm 276^c$ | $174 \pm 75^c$ |

[a]LacZ transduction was measured by X-Gal staining and by expressing the number of blue cell colonies as a function of the amount of p24 antigen in the inoculum
[b]eGFP transduction was measured by FACS analysis, multiplying the fraction of fluorescent cells by the number of infected cells, and expressing the result as a function of the amount of p24 antigen in the inoculum
[c]Luciferase transduction was measured by the luminescence in relative units above background (RLU) of 50 μl of culture extract and dividing the number of RLU $\times 10^{-3}$ by the number of ng of p24 antigen in the inoculum
[d]without internal promoter Vectors were produced by the transfection of the indicated transfer vector, a packaging construct either with (pCMVΔR8.91) or without (pCMVΔR8.93) a functional tat gene and the pMD.G plasmid into 293T cells. Serial dilutions of transfectant conditioned medium were incubated with the indicated cells, and the cultures were scored after 3 days. For calculating transduction activity, samples were selected from the linear portion of the vector dose response curve. The mean error of triplicate determinations are shown for a, c, d; and the mean of duplicate determinations is shown for b.

The tat-defective phenotype was tested to determine whether the phenotype could be rescued by complementation in target cells (Table 3). HeLa-tat cells, a cell line expressing Tat from the HIV-1 LTR. (Felker et al., J. Virol. (1990) 64: 3734-3741), were transduced by vectors produced with or without Tat. The expression of Tat in target cells did not compensate for the loss in transduction efficiency of vector produced without Tat.

As expected from the Northern analysis, functional inactivation of the tat gene resulted in a lower abundance of vector RNA in producer cells. That was indicated by the decrease in luciferase activity in cells producing a luciferase vector without internal promoter.

There, transgene expression directly reflects the abundance of transcripts originating from the LTR. 293T cells producing luciferase vectors without Tat had only 5% the luciferase content of cells producing the same vector with Tat ($1.0 \pm 2 \times 10^9$ RLU/dish without Tat: $20.2 \pm 0.7 \times 10^9$ RLU/dish with Tat). The ratio corresponded very closely to that observed in cells transduced by either type of vector in the course of the same experiment (see Table 3), suggesting that the abundance of vector RNA in producer cells is a rate-limiting factor in the transduction by lentiviral vectors.

It could be concluded that Tat is required in producer cells to activate transcription from the HIV LTR and to generate vector particles with a high transducing activity.

The tat requirement is offset by placing a constitutive promoter upstream of the transfer vector. If the only function of Tat is trans-activation of vector transcription from the LTR, the tat-defective phenotype should be rescued by placing a strong constitutive promoter upstream of the vector transcript. Three transcriptional domains have been identified in the HIV promoter in the U3 region of the LTR: the core or basal domain, the enhancer and the modulatory domain (Luciw, supra). Transcription starts at the U3/R boundary, the first nucleotide of R being numbered 1. The core promoter contains binding sites for the TATA-binding protein (−28 to –24) and SP-1 (three binding sites between –78 to –45). The enhancer contains two binding sites for NF-KB which overlap with a binding site for NFATc (–104 to –81). The modulatory domain contain binding sites for several cellular factors, including AP-1 (–350 to –293)., NFAT-1 (–256 to –218) USE-1 (–166 to –161), Ets-1 (–149 to –141) and LEE (–136 to –125). A panel of 5' chimeric transfer constructs carrying substitutions of either all or part of the U3 region of the 5' LTR was generated. All substitutions were made to preserve the transcription initiation site of HIV. Partial substitutions joined new enhancer sequences to the core promoter of the HIV LTR (–78 to 1), while full substitutions replaced also the promoter. RLL and RRL vectors carried the enhancer or the enhancer and promoter, respectively, of Rous sarcoma virus (RSV); and CLL and CCL vectors carried the enhancer or the enhancer and promoter of human CMV.

Control pHR2 and 5' chimeric transfer constructs carrying a PGK-eGEP expression cassette were tested by transfection of 293T cells with control or tat-defective packaging constructs and the expression of the eGFP transgene was analyzed by FACS. The RRL chimeric construct yielded higher eGFP expression level than the pHR2 vector reflecting the constitutive transcriptional activity of the new sequence. Interestingly, the chimeric vector also displayed upregulation by Tat as shown by the increased eGFP expression of cells cotransfected with the control packaging construct. Tat upregulation was proven to be a direct effect by transfecting a pRRL-eGFP vector lacking an internal promoter with control or tat-defective packaging constructs and analyzing GFP expression by FACS. Comparable results were obtained with the other chimeric LTR vectors. Vector particles then were collected from the transfected producer cells and assayed for transduction of eGFP into HeLa cells and human primary lymphocytes (PBL). As shown in Table 4, all vectors had efficient transducing activity, as assessed by end-point titration on HeLa cells, or maximal transduction frequency of PBL. The vector produced by the pRRL chimera was as efficient as that produced by the pHR2 construct and was selected to test transduction independent of Tat. As shown in Table 2, the pRRL construct yielded vector of only slightly reduced transducing activity (60%) when the packaging construct was tat-defective. The residual effect of Tat on transduction was in agreement with the ability of Tat to upregulate transcription from the chimeric LTR. Tat upregulation was proven to be a direct effect by transfecting a pRRL-eGFP vector lacking an internal promoter with control or tat-defective packaging constructs and analyzing GFP expression by FACS.

TABLE 4

GFP transduction by lentiviral vectors made by transfer constructs with wild-type or a 5' chimeric LTR

| Transfer Construct | End-Point Titer on HeLa cells (T.U./ml)[a] | Transduction Efficiency on Human Lymphocytes (% positive cells)[b] |
|---|---|---|
| pHR2 | 2.3 × 10[7] | 30% |
| PCCL | 4.6 × 10[6] | 14% |
| PCCL | 7.9 × 10[6] | 18% |
| PRRL | 1.8 × 10[7] | 29% |
| PRRL | 8.9 × 10[6] | 18% |

[a]end-point titer was determined by multiplying the percent of fluorescent cells for the vector dilution and the number of infected cells. Samples were selected from the linear portion of the vector dose-response curve
[b]percentage of fluorescent human peripheral blood lymphocytes after infection of 10[6] cells with 1 ml of vector containing medium. Primary human T lymphocytes were isolated and transduced as previously described (Finer et al., supra)

Vectors carrying a PGK-eGFP expression cassette were produced by the transfection of the indicated transfer construct, the packaging plasmid pCMVΔR8.91 and the envelope plasmid pMD.G into 293T cells. Fluorescent cells were scored by FACS analysis 6 days after transduction. The average of duplicate determination is shown for a representative experiment of three performed.

The use of the chimeric LTR construct allowed removal of Tat from the packaging system with a minimal loss in the transduction efficiency of the vector in vitro. To test vector performance in the more challenging setting of in vivo delivery into brain neurons, high-titer vector stocks were generated from the pHR2 and pRRL construct with and without Tat. The four stocks of eGFP vector were matched for particle content by p24 antigen and injected bilaterally in the neostriatum of groups of three adults rats. The animals were sacrificed after 1 month and serial sections of the brain were analyzed for eGFP fluorescence and immunostained by antibodies against eGFP. The results obtained in vivo matched the in vitro data. Vector produced by the pHR2 construct only achieved significant transduction of the neurons when packaged in the presence of Tat. Vector produced by the pRRL chimera was as well efficient when made with or without Tat. The transduction extended throughout most of the striatum and reached a very high density of positive cells in the sections closest to the injection site. No signs of pathology were detectable in the injected tissue, except for a small linear scar marking the needle track, by hematoxylin and eosin staining of the sections.

The results provide evidence that Tat is dispensable for efficient transduction by a lentiviral vector.

A split-genome conditional packaging system. The possibility of deleting the tat gene prompted design of another packaging component of the HIV vector system in which two separate non-overlapping expression plasmids, one for the gag-pol gene and the other for the rev gene, were used. The gag-pol reading frames were expressed within the context of the MD cassette, which employs the CMV promoter and intervening sequence and the human B globin poly (A) site (Ory et al., supra). All the HIV sequences upstream of the gag initiation codon were removed and the leader was modified for optimal fit to the Kozak consensus for translation. The construct, however, expressed almost no p24 antigen when transfected atone in 293T cells. That observation is in agreement with the previously reported presence of cis-repressive or inhibitory sequences in the gag/pol gene (Schneider et al., J. Virol. (1997) 71: 4892-4903; and Schwartz et al., J. Virol. (1992) δ 71767182). The HIV RRE element was then inserted downstream of the pot gene and the resulting plasmid was cotransfected with a rev expression vector (Table 5).

High levels of p24 antigen production were observed, the highest yields being obtained when rev was driven by an RSV promoter. When the gag/pot and the rev constructs were cotransfected with the RRL chimeric transfer vector and the VSV G-expressing plasmid, high titer vector was obtained in the culture medium. Both the yield of particles and their transducing efficiency were similar to those obtained with previous versions of the system. Northern analysis of producer cells confirmed that unspliced vector genomic RNA accumulated only in the presence of Rev. Thus, both the expression of the gag-pol genes and the accumulation of packageable vector transcripts are dependent on trans-complementation by a separate Rev expression construct. Such a conditional packaging system provides an important safety feature unavailable to oncoretroviral vectors.

TABLE 5

GFP transduction into HeLa cells by lentiviral vectors made by linked or split packaging constructs and a pRRL transfer construct.

| Packaging Construct | Separate rev Plasmid[a] | p24 Antigen (ng/ml) | End-point Titer (T.U./ml) | Transduction Efficiency (T.U./ng p24) |
|---|---|---|---|---|
| pCMVΔR8.74 | — | 364 | $1.07 \times 10^7$ | 29,436 |
| pMDLg/pRRE | — | <0.1 | N.D.[b] | N.A. |
| pMDLg/pRRE | TK-Rev 5 µg | 29 | $6.9 \times 10^5$ | 23,793 |
| pMDLg/pRRE | TK-Rev 12 µg | 94 | $2.02 \times 10^6$ | 21,489 |
| pMDLg/pRRE | RSV-Rev 2.5 µg | 774 | $1.0 \times 10^7$ | 13,495 |
| pMDLg/pRRE | RSV-Rev 5 µg | 776 | $7.6 \times 10^6$ | 9,761 |
| pMDLg/pRRE | RSV-Rev 12 µg | 565 | $4.8 \times 10^6$ | 8,495 |

[a]the promoter driving the expression of a synthetic rev cDNA and the amount of plasmid transfected are indicated Vectors carrying a PGK-eGFP expression cassette were produced by the transfection of a self-inactivating pRRL transfer construct (with a deletion in the 3' LTR 53), the indicated packaging and rev plasmids and the pMD.G plasmid into 293T cells. Serial dilutions of transfectant conditioned medium were incubated with HeLa cells and the cultures were scored after 6 days. For calculating end-point titer samples were selected from the linear portion of the vector dose response curve. The average of duplicate determination is shown for a representative experiment of three performed.
[b]N.D.: none detected. The detection limit of the assay was $10^2$ T.U./ml.

EXAMPLE 11

In another embodiment of the invention, pRRLsin36PGKGFPtet°3' is a lentivirus vector in which the 3' LTR contains a hybrid tet°/HIV U3. The 3' U3 consists of seven copies of the tet operator (tet°7) linked to the 3' 36 nucleotides of the HIV U3 including the "tata" box.

pRRLsin36PGKGFPtet°3' is a conditional self inactivating (SIN) vector that, after transduction, can be activated to express full-length packagable vector transcripts only in the presence of tet-transactivator (tta)—for example, after transduction of an appropriate tta expressing packaging cell line. After transduction of any cell not expressing tta, the resulting 5' tet°7/HIV U3 is essentially non-functional, even in the presence of HIV tat, significantly reducing the chance of mobilization of the vector genome. pRRLsin36PGKGFPtet°3' allows for a SIN vector which can be serially transduced ("pinged") into a tta-expressing packaging cell line to obtain a high-titer producer clone while maintaining the SIN phenotype in non-tta expressing target cells. To generate pRRLsin36PGKGFPtet°3', first a 5.6 kb Asp718-BamHI fragment from pRRL5sinI8PGKGFP was ligated to a 303 bp XhoI-Asp718 fragment from ptetsplice along with a DNA linker consisting of synthetic oligonucleotides 5'GATCCCGGGC-3' (SEQ ID NO: 49) and 5'-TCGAGCCCGG-3' (SEQ ID NO; 50) to generate ptetINT (pRRL5sinI8PGKGFP is a vector in which the untranslated region of pRRLsin18PGKGFP (Zufferey et al., J. Virol (1998) 72; 9873-9880) has been replaced with the corresponding region from pHR5). Next a 2.8 kp AflII-Asp718 fragment from ptetINT was ligated to a 3.1 kb BclI-AflII fragment from pRRLsin36PGKGFP (Zufferey et al. (1998) supra) along with a DNA linker consisting of synthetic oligonucleotide 5'-GTACCCGGGTCGAGTAGGCTT-3' (SEQ ID NO; 51) and 5'-GATCAAGCCTACTCGACCCGG-3' (SEQ ID NO: 52) to generate ptet361NT. Finally, a 3.4 kb BamHI-AflII fragment from ptet361NT was ligated to a 3.6 kb AflII-BclI fragment from pRRLsin36PGKGFP to yield pRRLsin36PGKGFPtet°3'.

Another such vector is maximally deleted in the 5' untranslated region. The 3' LTR of pCCL7sinCMVGFPpre has been replaced with the tet-responsive 3' LTR from pRRLsin36PGKGFPtet°3'. pCCL7sinCMVGFPpreTet°3' was generated by ligating a 3.44 kb AflII-EcoRI fragment from pCCL7sinCMVGFPpre with a 3.5 kb EcoRI-AflII fragment from pRRLsin36PGKGFPtet°3'.

EXAMPLE 12

To generate vector stocks containing a tetracycline inducible promoter sequence in the U3 region of the mRNA, the following plasmids were transfected: 10 µg of pRRLsin36PGKGFP, pRRLhPGKGFP or pRRLsin36PGKGFPtet; 6.5 µg of pMDLg/pRRE; and 3 µg of pMD.G into 293T cells. Vector stocks containing mRNA derived from the pRRLhPGKGFP construct served as a positive (non-regulatable) control. Vector stocks containing mRNA derived from the pRRLsin36PGKGFP construct served as a negative control (since on transduction, copying by reverse transcriptase (RT) of a deleted U3 region to the 5' region of the integrated vector DNA would render the resulting LTR transcriptionally non-functional).

Figure 10:
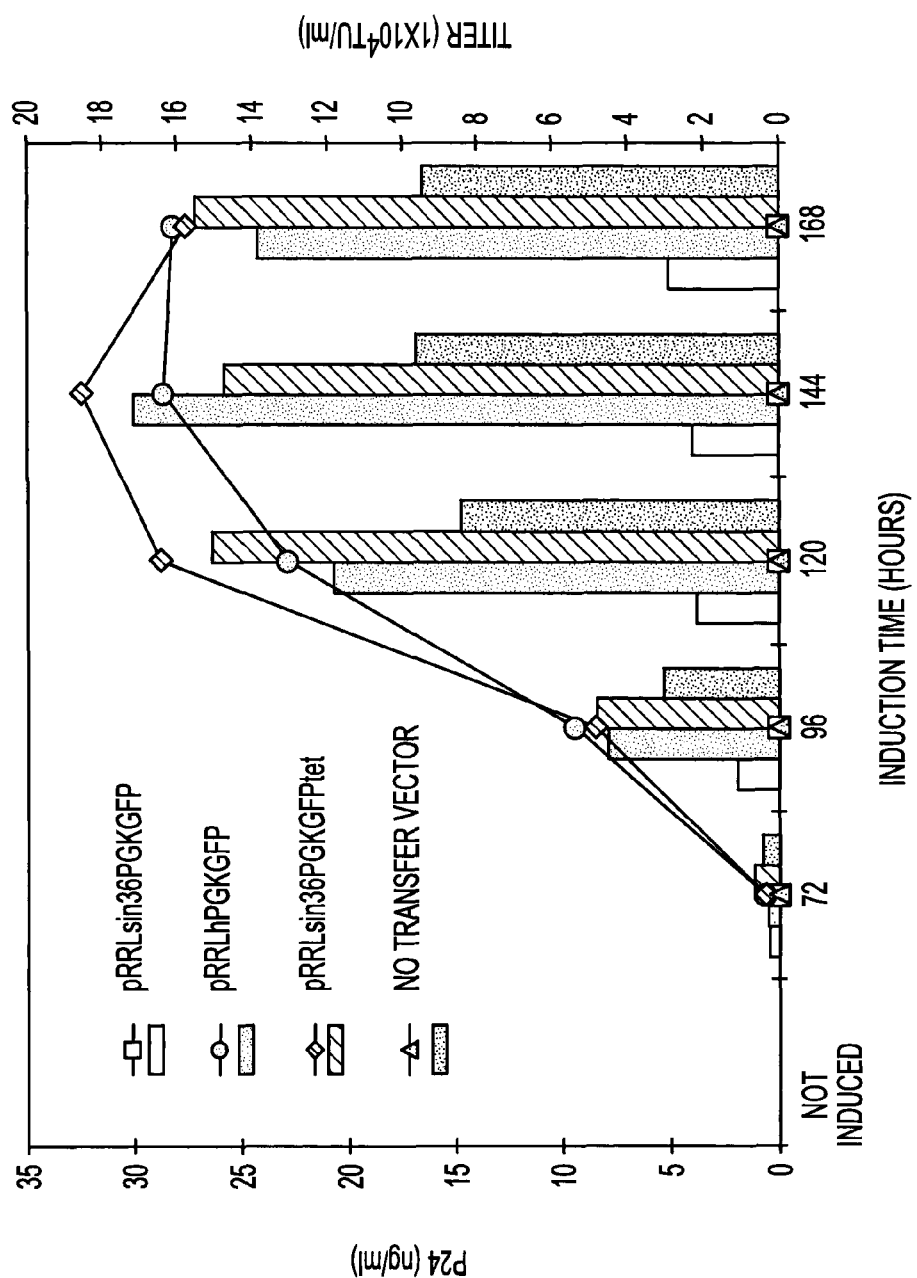
FIG. 10 depicts production and titer of vector particles produces by a 2"" generation packaging cell line (clone 2.54) pinged by a tetracycline regulatable transfer vector.

Supernatants of the transfected cells were collected, 0.22 micron pore size filtered and used for rounds of pinging of a 2nd generation packaging cell line at MOI=5 TU/cell (multiplicity of infection) each ping. Cells were cultured for an additional 2 weeks, split into 10 cm dishes at 50 to 70% confluence and induced for vector production by removing tetracycline from the medium. Supernatants of the induced promoter cells were collected as indicated in FIG. 10 and assayed for p24 and titer. Titer determination was done by infection of indicator HeLa cells with limited dilutions of assayed vector preparations. Percentage of transduced cells were scored by FACS.

As can be seen from FIG. 10, vector production and titers of vector particles for tetracycline regulatable transfer vectors were comparable to those of the positive control.

In contrast to an HIV-1 derived LTR, transcriptional activity of the LTR of such a vector in the cells lacking tTA was not detected by Northern analysis of transduced cells (FIG. 11), or when GFP expression levels were analyzed by FACS (FIG. 12) even on infection of transduced cells by the wild type HIV-1. Total RNA was extracted (by standard techniques) from transduced cells and assayed with $^{32}$P-labeled DNA probe. Probe was generated by a random priming kit (HighPrime, Boeringer Mannheim) using a BamHI-NotI fragment of the GFP coding sequence of plasmid pRRLsin-PGKGFP was the template.

Figure 11A:
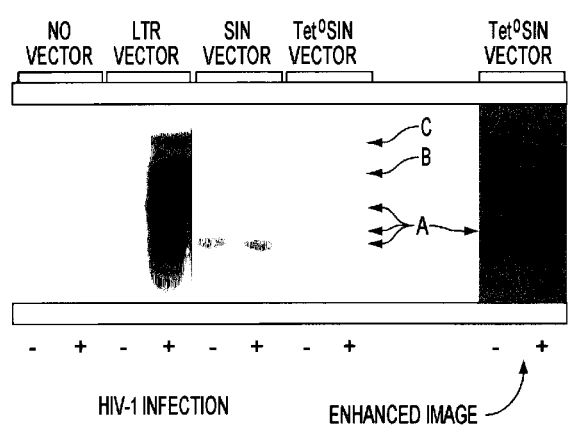
FIG. 11 depicts a representation of a Northern analysis of transduced HeLa cells using the indicated vectors. Total RNA was assayed with a GFP specific probe.
Figure 11B:
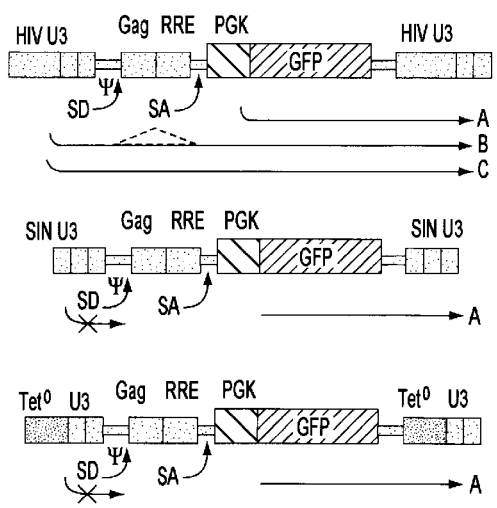
Figure 12A:
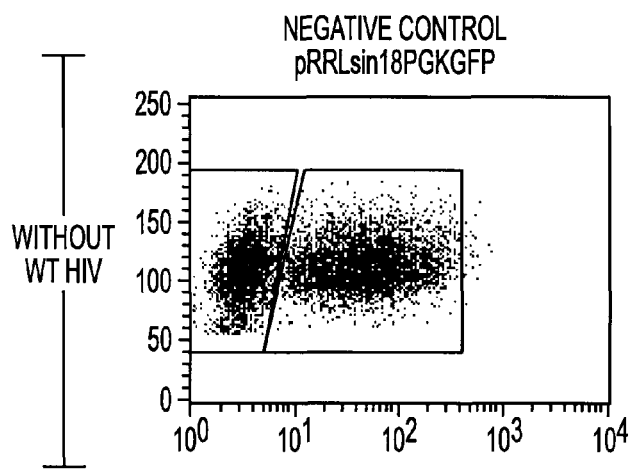
FIG. 12 depicts representations of FACS plots indicating that no activation of the Tet/HIV promoter takes place on HIV-1 infection.
Figure 12B:
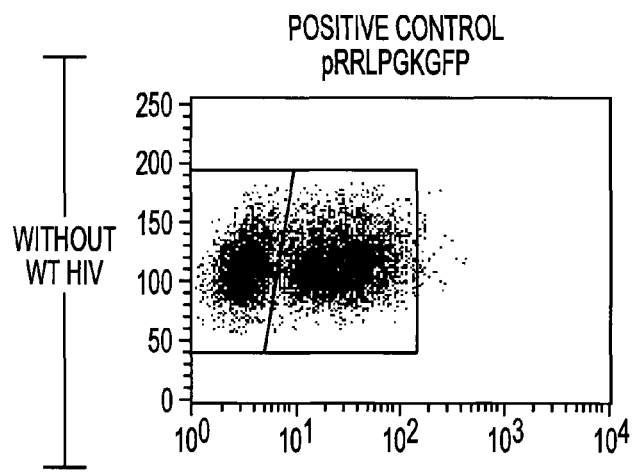
Figure 12C:
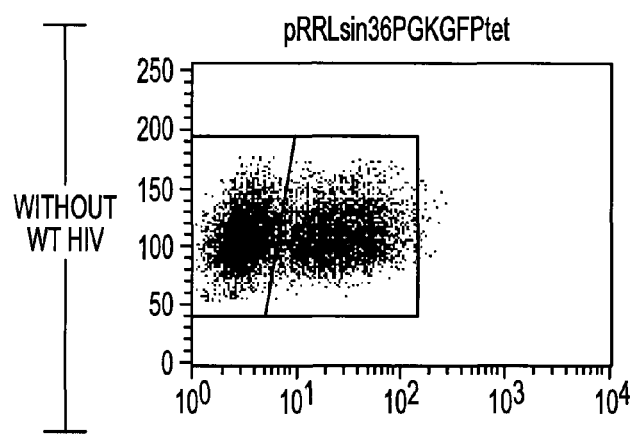
Figure 12D:
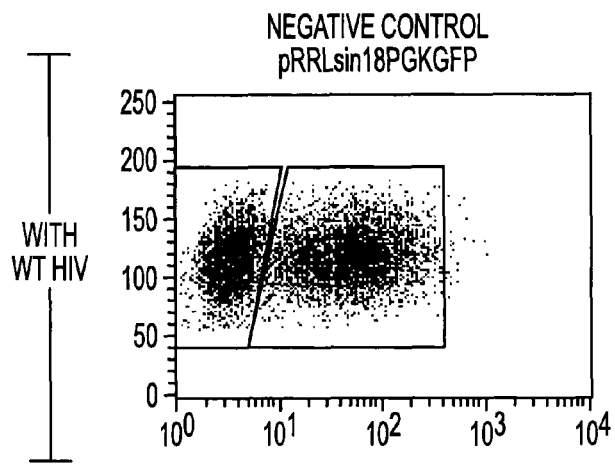
Figure 12E:
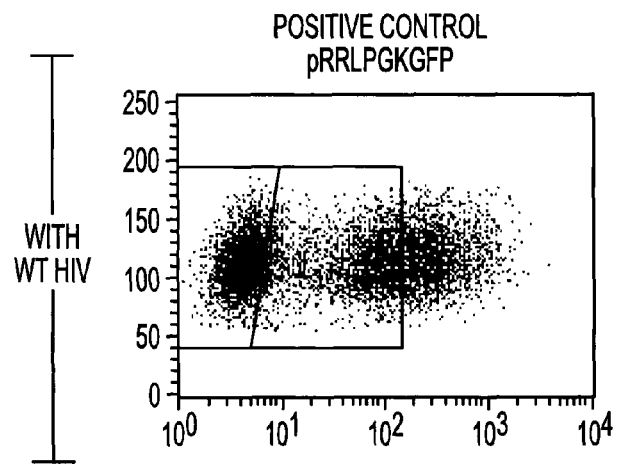
Figure 12F:
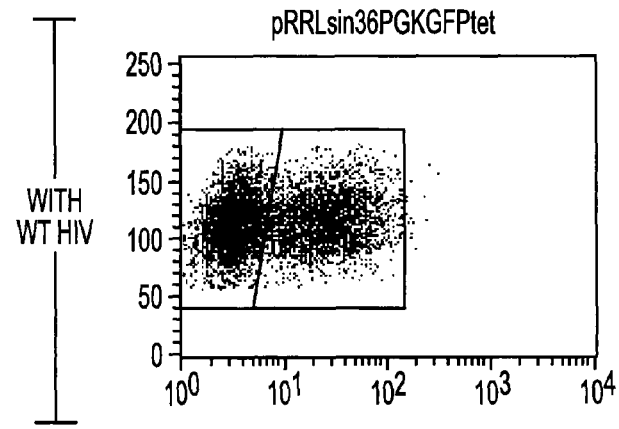

As can be seen in FIG. 11 in contrast to a vector with an HIV-1 LTR, no LTR driven mRNA could be detected for both the control and tetracycline responsive vectors. Consistent with those results, FACS analysis (FIG. 12) also showed that GFP expression was upregulated by HIV-1 infection only in cells transduced by the vector with a full length HIV-1 LTR. Thus, such regulatable vectors retain the SIN phenotype.

All publications and patents cited in the instant specification are herein incorporated by reference in their entirety as if each individual publication or patent application were specifically and individually indicated to be incorporated by reference.

As will be apparent to those skilled in the art to which the invention pertains, the instant invention may be embodied in forms other than those specifically disclosed above, for example to transfect and transduce other mammalian cell types, without departing from the spirit or essential characteristics of the invention. The particular embodiments of the invention described above, are, therefore, to be considered as illustrative and not restrictive. The scope of the instant invention is as set forth in the appended claims rather than being limited to the examples contained in the foregoing description.

We claim:

1. A lentiviral vector system comprising a lentiviral packaging system and a lentiviral transfer vector comprising a heterologous gene operably linked to a regulatory element,
   wherein the lentiviral packaging system comprises a structural lentiviral vector system comprising a first lentiviral vector that encodes a structural gene selected from a gag gene, a pol gene or both gag and pol genes,
   wherein the lentiviral transfer vector comprises a 5' LTR and a 3' LTR,
   wherein the regulatory element is a heterologous regulatory element operable in a mammalian cell,
   wherein a part or all of a regulatory element of the U3 region of the 5' LTR is replaced by the heterologous regulatory element,
   wherein a part of the U3 region of the 3' LTR is replaced by a heterologous inducible regulatory element that is activated only in the presence of an activator expressed in trans, wherein the replaced part of the U3 region of the 3' LTR includes sequences that span from nucleotide 418 up to nucleotide 36, wherein the heterologous inducible regulatory element is linked to a part of the 3' U3 region that comprises a TATA box sequence,
   wherein the lentivirus is human immunodeficiency virus (HIV),
   and wherein said lentiviral vector system achieves the titer of vector particles not lower than $1 \times 10^5$ TU/ml.

2. The lentiviral vector system of claim 1, wherein the HIV is HIV-1.

3. The lentiviral vector system of claim 1, wherein the heterologous inducible regulatory element comprises a tet operator.

4. The lentiviral vector system of claim 3, wherein the heterologous inducible regulatory element comprises seven copies of a tet operator (tet 7).

5. The lentiviral vector system of claim 1, wherein the structural lentiviral vector system further comprises a regulatory response element (RRE) downstream of the structural gene.

6. The lentiviral vector system of claim 1, wherein the structural lentiviral vector system further comprises a heterologous regulatory element operably linked to the structural gene.

7. The lentiviral vector system of claim 6, wherein the heterologous regulatory element operably linked to the structural gene comprises a cytomegalovirus (CMV) promoter.

8. The lentiviral vector system of claim 1, which lacks a functional tat gene.

9. The lentiviral vector system of claim 8, wherein the tat gene is deleted.

10. The lentiviral vector system of claim 8, wherein the tat gene is mutated.

11. The lentiviral vector system of claim 1, which lacks a functional HIV env gene.

12. The lentiviral vector system of claim 1, further comprising a viral env gene that is derived from a different virus than the structural genes.

13. The lentiviral vector system of claim 12, wherein the env gene is provided on a vector other than the first lentiviral vector.

14. The lentiviral vector system of claim 1, which lacks functional vif, vpr, vpu and nef genes.

15. A method of producing a recombinant lentivirus comprising:
   (a) transfecting a packaging host cell with the lentiviral vector system of claim 1; and
   (b) recovering the recombinant lentivirus produced by the transfected packaging host cell.

16. The lentiviral vector system of claim 1, wherein the lentiviral packaging system further comprises a regulatory lentiviral vector comprising a rev gene, and wherein the regulatory lentiviral vector is provided on a separate construct from the structural lentiviral vector.

17. The lentiviral vector system of claim 1, wherein the gag gene is mutated.

18. A method of producing a recombinant lentivirus comprising:
   (a) transfecting a packaging host cell with the lentiviral vector system of claim 2; and
   (b) recovering the recombinant lentivirus produced by the transfected packaging host cell.

19. A method of producing a recombinant lentivirus comprising:
   (a) transfecting a packaging host cell with the lentiviral vector system of claim 16; and
   (b) recovering the recombinant lentivirus produced by the transfected packaging host cell.

20. The lentiviral vector system of claim 16, wherein the regulatory lentiviral vector further comprises a heterologous regulatory element operably linked to the rev gene.

21. The lentiviral vector system of claim 20, wherein the heterologous regulatory element operably linked to the rev gene comprises a Rous sarcoma virus (RSV) U3 or a herpes simplex virus thymidine kinase (HSVtk) promoter.

* * * * *